United States Patent
Ergun et al.

(10) Patent No.: US 8,967,560 B2
(45) Date of Patent: Mar. 3, 2015

(54) CAM BALANCE MECHANISM SYSTEMS AND METHODS

(75) Inventors: Mustafa A. Ergun, Plymouth, MN (US); Robert W. Fluhrer, Prior Lake, MN (US); Thiem Wong, Minneapolis, MN (US); Saeb Asamarai, Columbia Heights, MN (US); John Cain, St. Cloud, MN (US)

(73) Assignee: Ergotron, Inc., St. Paul, MN (US)

( * ) Notice: Subject to any disclaimer, the term of this patent is extended or adjusted under 35 U.S.C. 154(b) by 218 days.

(21) Appl. No.: 13/191,182

(22) Filed: Jul. 26, 2011

(65) Prior Publication Data

US 2012/0187256 A1  Jul. 26, 2012

Related U.S. Application Data

(60) Provisional application No. 61/369,430, filed on Jul. 30, 2010, provisional application No. 61/369,392, filed on Jul. 30, 2010.

(51) Int. Cl.
*F16M 11/04* (2006.01)
*F16M 11/20* (2006.01)
(Continued)

(52) U.S. Cl.
CPC ............ *F16M 11/2021* (2013.01); *A47B 9/12* (2013.01); *F16M 13/022* (2013.01); *F16M 11/24* (2013.01); *F16M 2200/048* (2013.01)
USPC ........ 248/161; 108/147; 248/404; 248/162.1; 248/572

(58) Field of Classification Search
CPC ........... A61B 6/00; A61B 6/08; F16M 11/00; F16M 11/04; A47B 21/0073
USPC ............... 248/123.11, 281.11, 919, 920, 562, 248/566, 572, 575, 577, 584, 600, 161, 248/162.1, 332, 404, 422; 108/147
See application file for complete search history.

(56) References Cited

U.S. PATENT DOCUMENTS

| 39,602 | A | * | 8/1863 | Whipple | ................. | 248/411 |
| 151,083 | A | * | 5/1874 | Buck | ..................... | 248/572 |

(Continued)

FOREIGN PATENT DOCUMENTS

| CN | 1713839 A | | 12/2005 |
| DE | 1091279 | * | 10/1960 |

(Continued)

OTHER PUBLICATIONS

International Search Report and Written Opinion for International Application No. PCT/US11/45369, dated Jan. 4, 2012, 16 pages.

(Continued)

*Primary Examiner* — Terrell McKinnon
*Assistant Examiner* — Eret McNichols
(74) *Attorney, Agent, or Firm* — Schwegman Lundberg & Woessner, P.A.

(57) ABSTRACT

Embodiments include a balance mechanism having a first cam and a second cam configured to convert a variable force exerted by the energy storage member into a substantially constant force applied to a mounting portion. The balance mechanism may be useful for balancing forces such that a user can set the height of an electronic display and/or other equipment attached to the balance mechanism at a number of heights within the range of travel allowed by the mechanism. Lift mechanisms, display positioning apparatuses, and height adjustable desks incorporating a multi-cam balance mechanism are also provided. A method of positioning a display is also provided.

41 Claims, 28 Drawing Sheets

(51) Int. Cl.
 *A47B 9/12* (2006.01)
 *F16M 13/02* (2006.01)
 *F16M 11/24* (2006.01)

(56) References Cited

U.S. PATENT DOCUMENTS

| | | | |
|---|---|---|---|
| 2,168,209 A | 8/1939 | Haupt et al. | |
| 2,713,530 A | 7/1955 | Chisholm | |
| 2,876,362 A | 3/1959 | Foderaro | |
| 3,517,625 A | 6/1970 | Swett et al. | |
| 3,575,368 A | 4/1971 | Thomas et al. | |
| 3,741,131 A | 6/1973 | Leadbetter | |
| 3,896,744 A | 7/1975 | Goebl | |
| 4,496,200 A | 1/1985 | Hagstrom et al. | |
| 4,533,096 A | 8/1985 | Baker | |
| 4,852,500 A | 8/1989 | Ryburg et al. | |
| 5,114,109 A * | 5/1992 | Fitz et al. | 248/404 |
| 5,174,223 A | 12/1992 | Nagy | |
| 5,277,392 A | 1/1994 | Rossman et al. | |
| 5,381,738 A | 1/1995 | Meyer et al. | |
| 5,400,721 A | 3/1995 | Greene | |
| 5,484,124 A | 1/1996 | Billings et al. | |
| 5,537,289 A | 7/1996 | Dahl et al. | |
| 5,568,773 A | 10/1996 | Hung | |
| 5,630,566 A | 5/1997 | Case | |
| 5,735,222 A | 4/1998 | Webb et al. | |
| 5,765,797 A | 6/1998 | Greene | |
| 5,918,841 A | 7/1999 | Sweere et al. | |
| 5,975,469 A | 11/1999 | Chen | |
| 6,042,064 A | 3/2000 | Hong | |
| 6,042,075 A | 3/2000 | Burch, Jr. | |
| 6,085,665 A | 7/2000 | Smith et al. | |
| 6,196,354 B1 | 3/2001 | Anthony et al. | |
| 6,208,505 B1 | 3/2001 | Kuchta et al. | |
| 6,332,407 B1 | 12/2001 | Vardaro | |
| 6,374,752 B1 | 4/2002 | Walser | |
| 6,434,851 B1 | 8/2002 | Nishina | |
| 6,517,040 B1 | 2/2003 | Wen et al. | |
| 6,536,728 B1 | 3/2003 | Hagglund et al. | |
| 6,637,350 B2 | 10/2003 | McKsymick | |
| 6,712,008 B1 | 3/2004 | Habenicht et al. | |
| 6,994,306 B1 | 2/2006 | Sweere | |
| 6,997,422 B2 | 2/2006 | Sweere | |
| 7,032,523 B2 | 4/2006 | Forslund, III et al. | |
| 7,178,469 B2 | 2/2007 | Goza | |
| 7,252,277 B2 | 8/2007 | Sweere | |
| 7,506,853 B2 | 3/2009 | Sweere | |
| 7,546,811 B2 | 6/2009 | Owen et al. | |
| 7,677,518 B2 | 3/2010 | Chouinard | |
| 7,823,973 B2 | 11/2010 | Dragusin et al. | |
| 7,997,211 B2 | 8/2011 | Peterson | |
| 8,191,487 B2 | 6/2012 | Theesfeld et al. | |
| 8,826,831 B2 | 9/2014 | Hazzard et al. | |
| 8,839,723 B2 | 9/2014 | Hazzard et al. | |
| 2004/0188573 A1 | 9/2004 | Weatherly et al. | |
| 2004/0194669 A1 | 10/2004 | Forslund, III et al. | |
| 2004/0250635 A1 | 12/2004 | Sweere | |
| 2005/0184215 A1 | 8/2005 | Lin | |
| 2005/0217540 A1 | 10/2005 | Novak | |
| 2006/0096505 A1 * | 5/2006 | Sykes | 108/50.01 |
| 2006/0130714 A1 | 6/2006 | Jones et al. | |
| 2006/0145036 A1 * | 7/2006 | Jones et al. | 248/188.5 |
| 2006/0185563 A1 | 8/2006 | Sweere | |
| 2006/0278770 A1 | 12/2006 | MacLeod | |
| 2007/0001076 A1 | 1/2007 | Asamarai | |
| 2007/0139870 A1 | 6/2007 | Lin | |
| 2007/0259554 A1 | 11/2007 | Lindblad | |
| 2008/0026892 A1 | 1/2008 | Asamarai | |
| 2008/0232059 A1 | 9/2008 | Allen | |
| 2009/0179121 A1 | 7/2009 | Lindblad | |
| 2010/0132122 A1 | 6/2010 | Hollingshead | |
| 2012/0187056 A1 | 7/2012 | Hazzard et al. | |
| 2013/0341476 A1 | 12/2013 | Hazzard et al. | |

FOREIGN PATENT DOCUMENTS

| | | |
|---|---|---|
| DE | 1611809 A1 * | 1/1971 |
| DE | 3610612 A1 * | 10/1987 |
| DE | 19635236 C1 * | 3/1998 |
| DE | 10252931 B3 * | 7/2004 |
| EP | 0481159 A1 | 4/1992 |
| JP | 2004033415 A * | 2/2004 |
| JP | 2013/535287 A | 9/2013 |
| JP | 2013535287 A | 9/2013 |
| WO | WO-2012015821 A1 | 2/2012 |

OTHER PUBLICATIONS

Ergotron, WorkFit C-Mod, Single LCD Mount, LD, "Dimensional and Range of Motion Illustrations", Aug. 2009, 4 pages.
Ergotron, "StyleView HD Combo" Product Sheet, Oct. 2009, 2 pages.
Ergotron HD Series Arms, "Height Adjustable Systems" Product Sheet, Sep. 2007, 2 pages.
Ergotron LX, "LX Wall Mount System" Dimensional Illustrations, Dec. 2006, 3 pages.
Ergotron 200 Series, "Combination Flat Panel/Keyboard Arm" Product Sheet, Aug. 2006, 2 pages.
Geek Reviews, "Ergodesktop's Kangeroo, An Adjustable Stand Up Desk," retrieved through http://www.geekculture.com/blurbs/reviews/kangaroo.html on Aug. 26, 2010, 4 pages.
Ergo Desktop, "The Wallaby," Copyright 2009, retrieved through http://www.ergodesktop.com/content/wallaby, Jul. 29, 2010, 3 pages.
Ergo Desktop, "Product Comparison," Copyright 2009, retrieved through http://www.ergodesktop.com/content/product-comparison, Jul. 29, 2010, 3 pages.
Ergo Desktop, "The Kangaroo Elite," Copyright 2009, retrieved through http://www.ergodesktop.com/content/kangaroo-elite, Jul. 29, 2010, 3 pages.
Ergo Desktop, "The Kangaroo Pro," Copyright 2009, retrieved through http://www.ergodesktop.com/content/kangaroo-pro, Jul. 29, 2010, 3 pages.
Ergo Desktop, "The Kangaroo," Copyright 2009, retrieved through http://www.ergodesktop.com/content/kangaroo-0#, Jul. 29, 2010, 3 pages.
Ergotron, "Ergotron 45-216-216 StyleView HD Combo System," retrieved through http://www.ergotron.com/Products/tabid/65/PRDID/270/language/en-US/Default.aspx, Jul. 8, 2010, 3 pages.
Ergotron, "WorkFit LD Assembly Instructions," May 2009, 15 pages.
Ergotron, "WorkFit C-Mod" Product Sheet, Nov. 2009, 2 pages.
Ergo Desktop, "Frequently Asked Questions," Copyright 2009, retrieved from http://www.ergodesktop.com/content/frequently-asked-questions, Jul. 29, 2010, 3 pages.
International Search Report and Written Opinion for International Application No. PCT/US11/45370, dated Dec. 23, 2011, 9 pages.
U.S. Appl. No. 13/191,170, Examiner Interview Summary mailed Jun. 10, 2013, 3 pgs.
U.S. Appl. No. 13/191,170, Examiner Interview Summary mailed Oct. 24, 2013, 2 pgs.
U.S. Appl. No. 13/191,170, Non Final Office Action mailed Feb. 1, 2013, 9 pgs.
U.S. Appl. No. 13/191,170, Non Final Office Action mailed May 1, 2014, 6 pgs.
U.S. Appl. No. 13/191,170, Non Final Office Action mailed May 29, 2014, 5 pgs.
U.S. Appl. No. 13/191,170, Non Final Office Action mailed Sep. 17, 2013, 7 pgs.
U.S. Appl. No. 13/191,170, Notice of Allowance mailed Jan. 30, 2014, 7 pgs.
U.S. Appl. No. 13/191,170, Notice of Allowance mailed Jul. 17, 2013, 8 pgs.
U.S. Appl. No. 13/191,170, Notice of Allowance mailed Aug. 1, 2014, 5 pgs.
U.S. Appl. No. 13/191,170, Response filed Jan. 9, 2013 to Restriction Requirement mailed Dec. 14, 2012, 2 pgs.
U.S. Appl. No. 13/191,170, Response filed May 19, 2014 to Non Final Office Action mailed May 1, 2014, 10 pgs.

(56) References Cited

OTHER PUBLICATIONS

U.S. Appl. No. 13/191,170, Response filed Jun. 27, 2013 to Non Final Office Action mailed Feb. 1, 2013, 20 pgs.
U.S. Appl. No. 13/191,170, Response filed Jul. 17, 2014 to Non Final Office Action mailed May 29, 2014, 9 pgs.
U.S. Appl. No. 13/191,170, Response filed Dec. 18, 2013 to Non Final Office Action mailed Sep. 17, 2013, 16 pgs.
U.S. Appl. No. 13/191,170, Restriction Requirement mailed Dec. 14, 2012, 7 pgs.
U.S. Appl. No. 13/964,870, Final Office Action mailed Feb. 25, 2014, 6 pgs.
U.S. Appl. No. 13/964,870, Non Final Office Action mailed Oct. 1, 2013, 9 pgs.
U.S. Appl. No. 13/964,870, Notice of Allowance mailed May 14, 2014, 6 pgs.
U.S. Appl. No. 13/964,870, Preliminary Amendment filed Aug. 12, 2013, 6 pgs.
U.S. Appl. No. 13/964,870, PTO Response to Rule 312 Communication mailed Aug. 18, 2014, 2 pgs.
U.S. Appl. No. 13/964,870, Response filed Feb. 3, 2014 to Non Final Office Action mailed Oct. 1, 2013, 11 pgs.
U.S. Appl. No. 13/964,870, Response filed Apr. 11, 2014 to Final Office Action mailed Feb. 25, 2014, 6 pgs.
Australian Application Serial No. 2011282862, Amendment filed Jul. 23, 2013, 101 pgs.
Australian Application Serial No. 2011282862, Subsequent Examiners Report mailed Aug. 11, 2014, 3 pgs.
European Application Serial No. 11813049.1, Extended European Search Report mailed Jul. 21, 2014, 7 pgs.
European Application Serial No. 11813049.1, Office Action mailed May 10, 2013, 2 pgs.
International Application Serial No. PCT/US2011/045369, International Preliminary Report on Patentability mailed Feb. 14, 2013, 13 pgs.
Australian Application Serial No. 2011282862, Examiners Report mailed Apr. 22, 2014, 3 pgs.
Australian Application Serial No. 2011282862, Response filed Aug. 8, 2014 to Examiners Report mailed Apr. 22, 2014, 197 pgs.
"Japanese Application Serial No. 2013-523197, Office Action mailed Jul. 14, 2010", (w/ English Translation), 10 pgs.

* cited by examiner

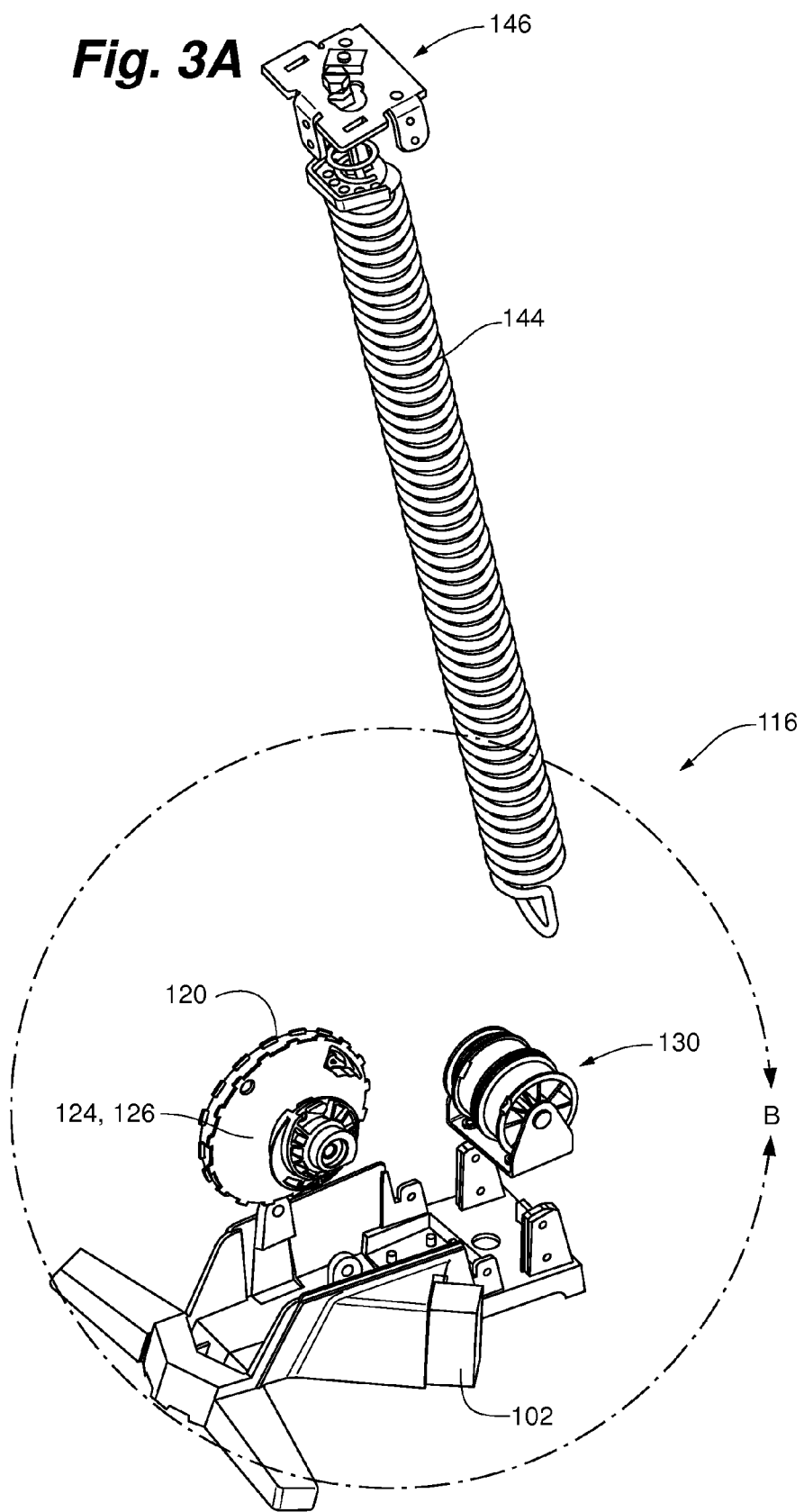

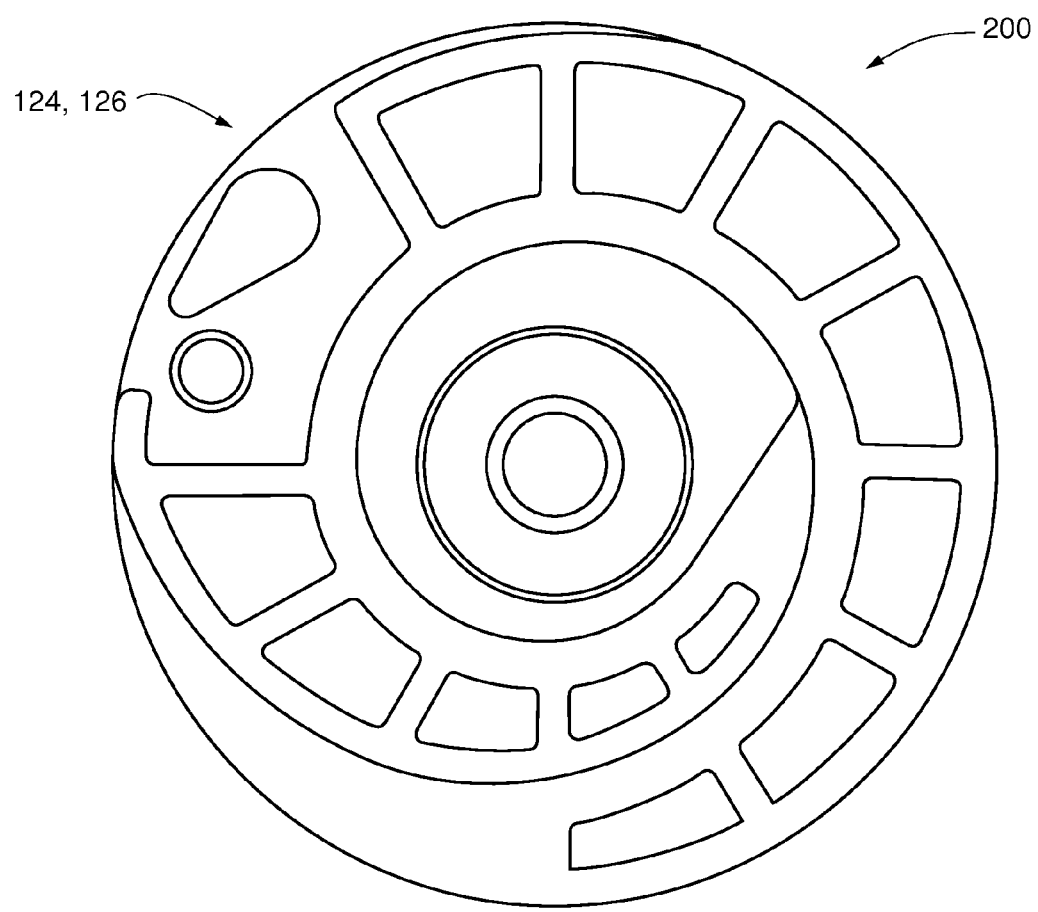

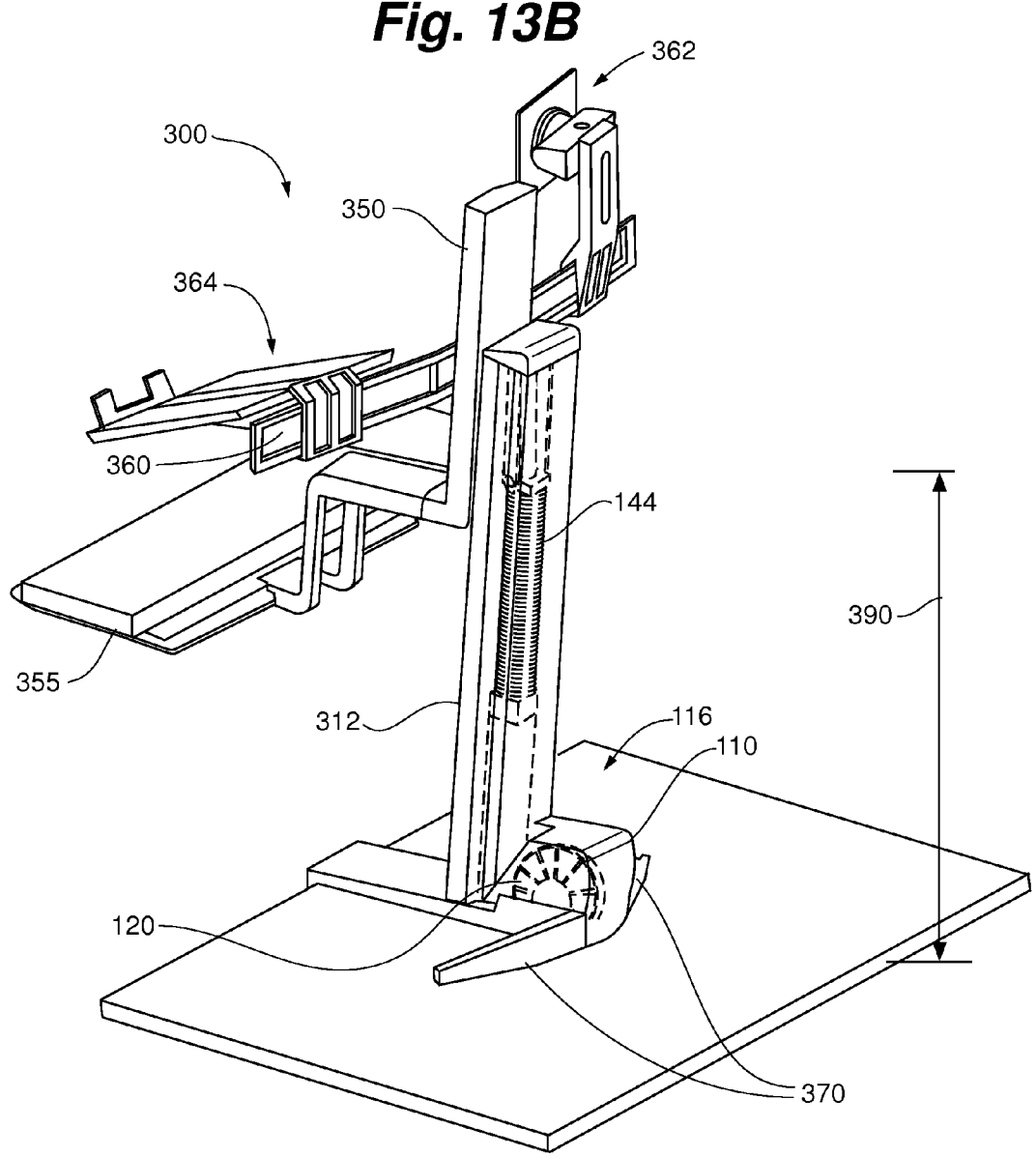

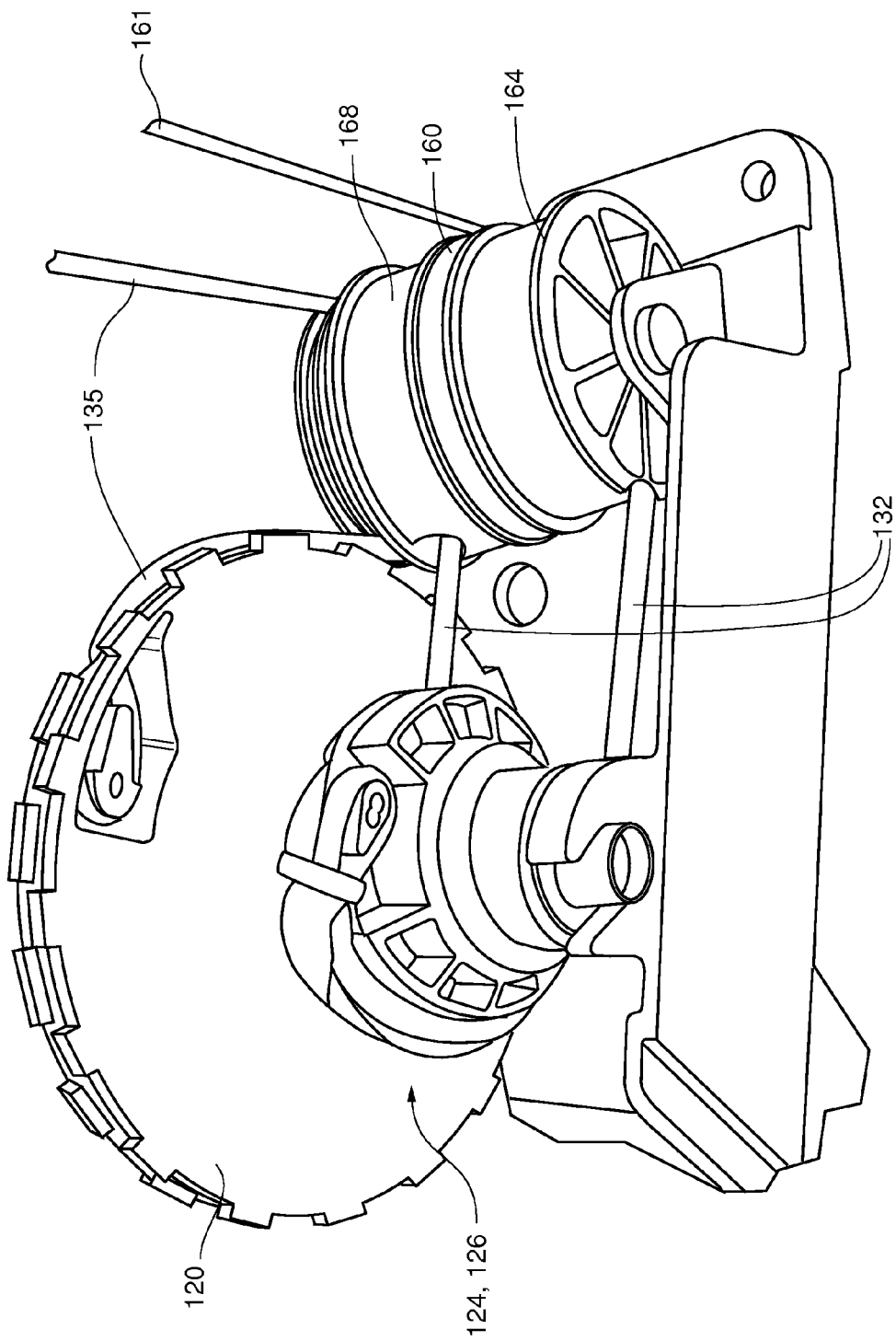

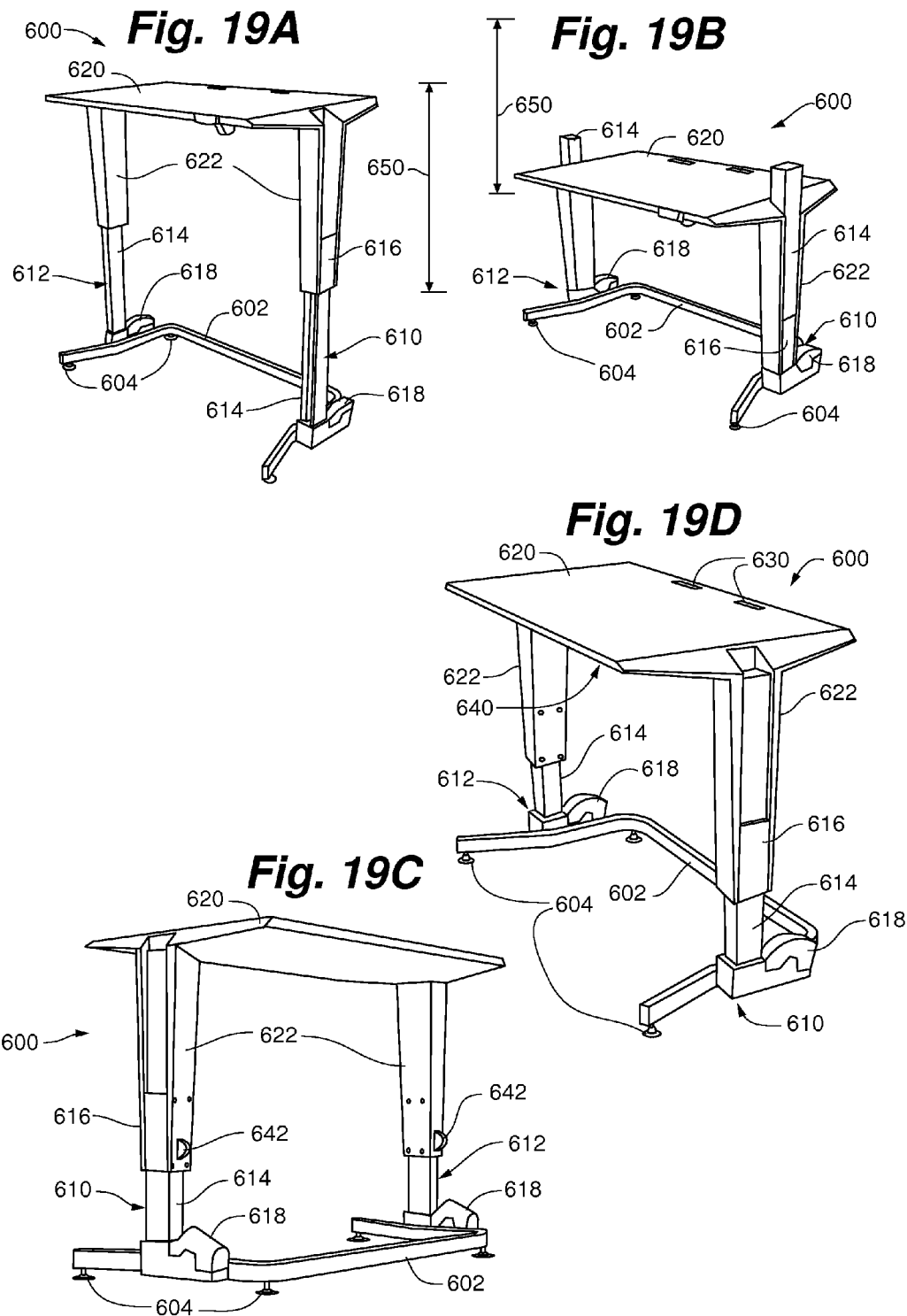

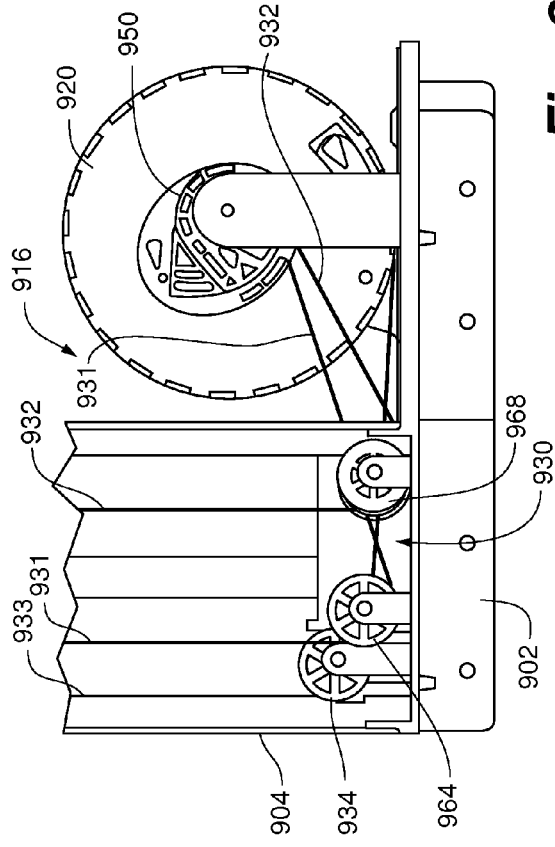
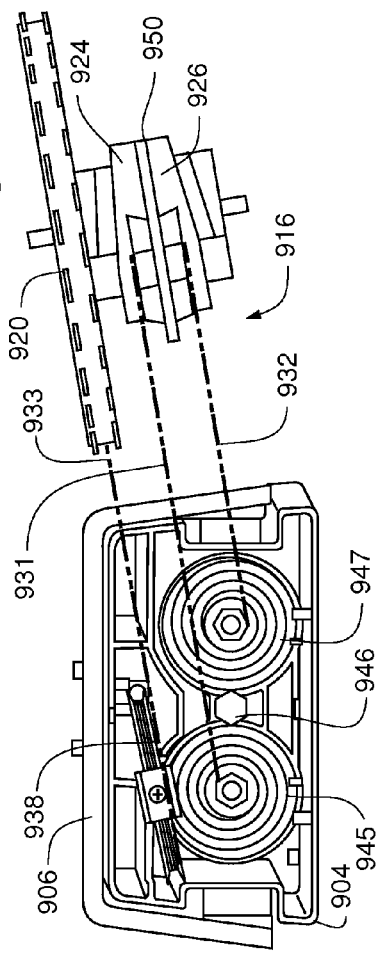
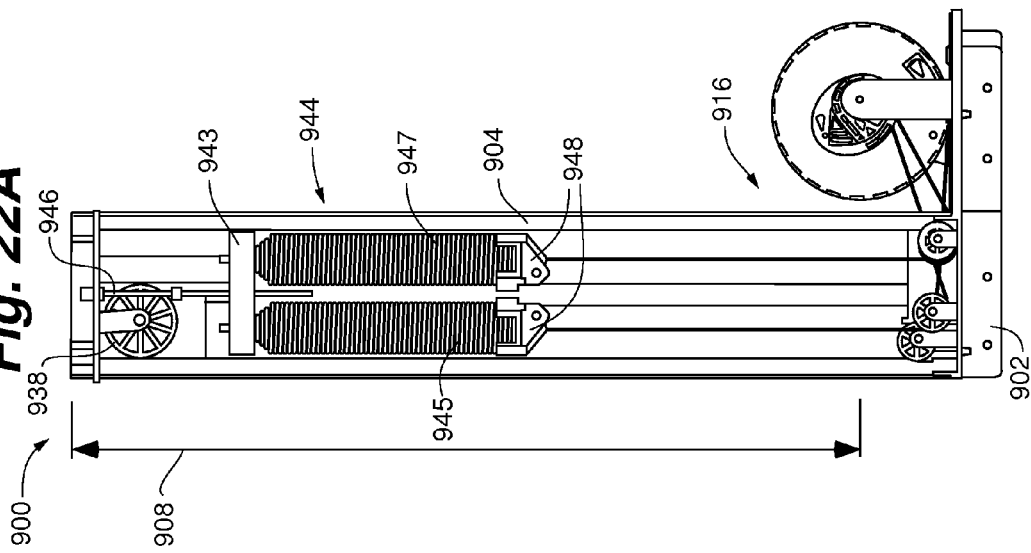

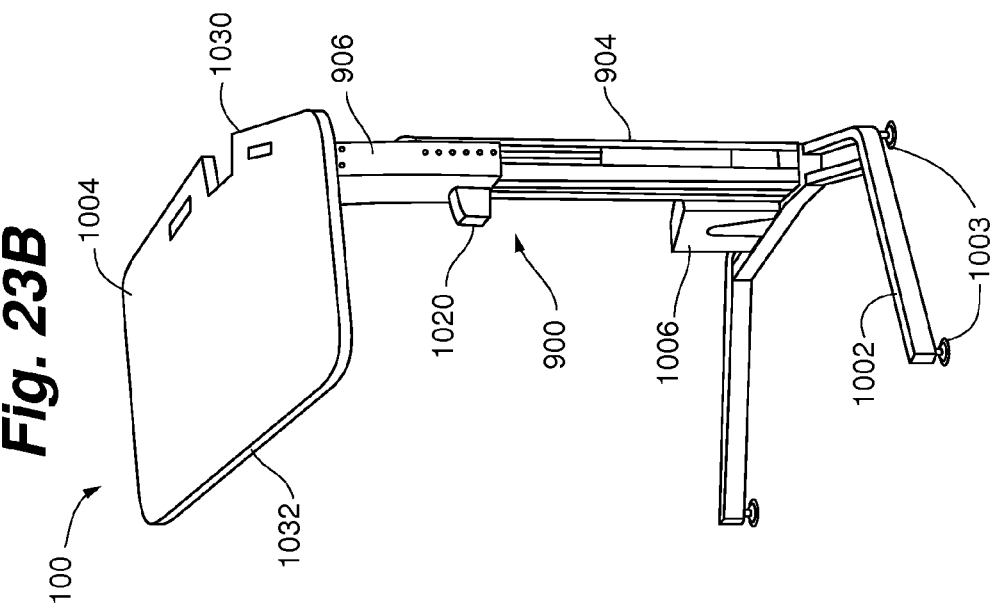
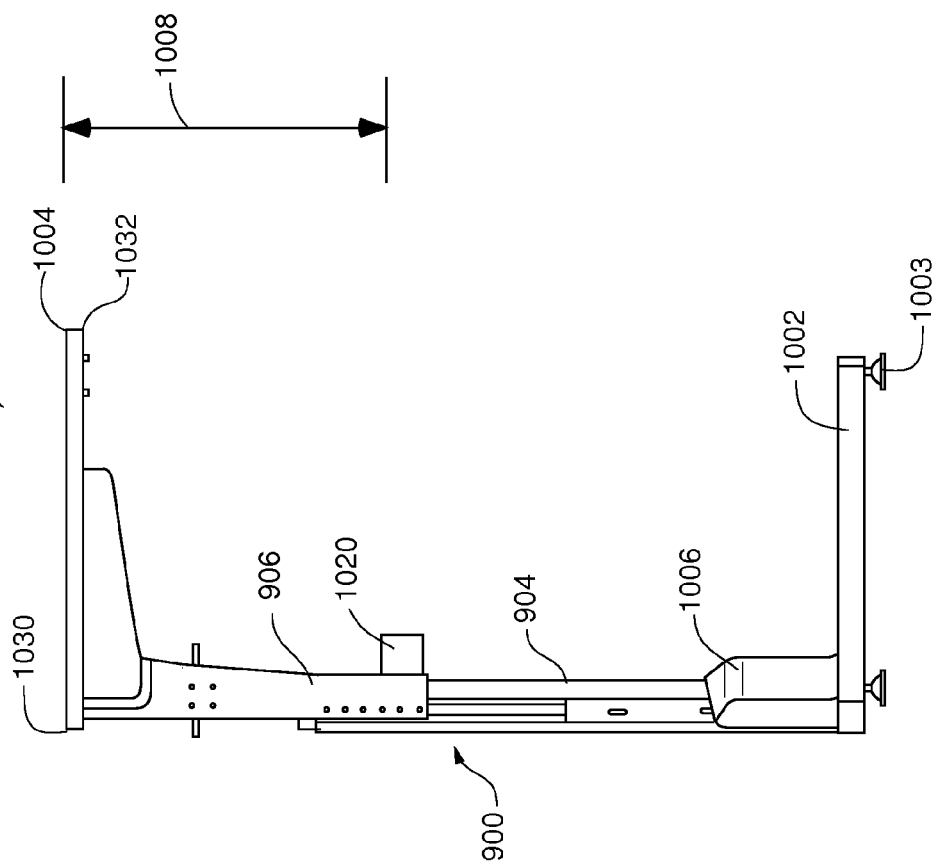

CAM BALANCE MECHANISM SYSTEMS AND METHODS

CROSS-REFERENCES

This application claims the benefit of U.S. Provisional Application No. 61/369,430, filed Jul. 30, 2010, and U.S. Provisional Application No. 61/369,392, filed Jul. 30, 2010, the content each of which is hereby incorporated by reference in its entirety.

FIELD

Embodiments of the invention generally relate to an apparatus for balancing a load.

BACKGROUND

Load balancing mechanisms are often incorporated in devices that provide adjustable positioning of one or more types of equipment. Such mechanisms can be useful for adjusting forces within a positioning device that would otherwise vary depending upon, for example, the particular load or the particular position of the load within a range of movement provided by the positioning device. Some articulated positioning devices include load balancing mechanisms particularly in order to assist an operator with manual positioning of different types of equipment.

One example of a positioning device that may incorporate a load balancing mechanism is a device for positioning an electronic display (e.g., monitor, television, etc.) and/or a computer. Many jobs involve working with personal computers and/or display monitors. In such jobs, the personal computers and/or display monitors may be used by multiple operators at different times during a day. In some settings, one computer and/or monitor may be used by multiple people of different sizes and having different preferences in a single day. Given the differences in people's size and differences in their preferences, a monitor or display adjusted at one setting for one individual may be inappropriate for another individual. For instance, a child would have different physical space needs than an adult using the same computer and monitor. Further, a single user may wish to periodically adjust the position of a display and/or other equipment in order to perform operations in various postures.

For equipment requiring frequent manual adjustment, lift assistance has been provided using gas springs, extension springs, and other types of energy providing devices. However, gas springs are costly and wear out over time. In addition, gas springs usually require a significant amount of space, for instance arm length, which can be at a premium in certain applications. In addition, some types of wire springs provide lift assistance that varies depending upon the extent of the spring compression or extension, which can provide uneven assistance through the range of movement and make some movements more difficult for manual operators.

As adjustable height mechanisms for displays have become more widespread and users have experienced their advantages, users are more frequently adjusting the height of their monitors and other equipment. Further, such adjustments are now more frequently desired over a wide range of travel. Moreover, as equipment grows in size and weight, ease of adjustability is an important consideration. While current load balancing mechanisms can address some of these issues, there is a continuing desire to increase weight capacity and/or reduce the size of positioning devices in order to accommodate bigger equipment. In addition, there is a desire for load balancing mechanisms and positioning devices which are compact, less costly to manufacture and maintain, have increased reliability, allow easy adjustability, are scalable to many different sized monitors, are adaptable to provide a long range of travel, and/or are adaptable to provide constant support force as the equipment is being positioned.

SUMMARY

Embodiments of the invention balancing a load, and more particularly relate to balancing forces from a source of variable forces in order to provide substantially constant forces. According to one aspect of the invention, a lift mechanism is provided that includes a base, a support column coupled to the base, a mounting portion movably coupled to the support column, an energy storage member coupled to the support column, and a balance mechanism coupled between the energy storage member and the mounting portion. The balance mechanism includes a first cam, a second cam rotationally coupled to the first cam, and a wheel rotationally coupled to the first cam and the second cam, wherein the first cam and the second cam are configured to convert a variable force exerted by the energy storage member into a substantially constant force applied to the mounting portion.

According to another aspect of the invention, a display positioning apparatus comprising is providing. The display positioning apparatus includes a base, a support column coupled to the base, a mounting portion movably coupled to the support column, the mounting portion comprising a display mount for attaching an electronic display, an energy storage member coupled to the support column, and a balance mechanism coupled between the energy storage member and the mounting portion. The balance mechanism includes a first cam, a second cam rotationally coupled to the first cam, and a wheel rotationally coupled to the first cam and the second cam, wherein the first cam, the second cam and the wheel are coaxially mounted to the base and the first cam and the second cam are configured to convert a variable force exerted by the energy storage member into a substantially constant force applied to the mounting portion.

Another aspect of the invention provides a height adjustable desk. The desk includes a base, a work surface, and at least one lift mechanism coupled between the base and the work surface. The at least one lift mechanism includes a support column coupled to the base, a mounting portion movably coupled to the support column and fixedly coupled to the work surface, an energy storage member coupled to the support column, and a balance mechanism coupled between the energy storage member and the mounting portion. The balance mechanism includes a first cam, a second cam rotationally coupled to the first cam, and a wheel rotationally coupled to the first cam and the second cam, wherein the first cam and the second cam are configured to convert a variable force exerted by the energy storage member into a substantially constant force applied to the mounting portion.

Another aspect of the invention provides a method of positioning a display. The method includes lifting a display within a vertical range of travel, assisting the lifting of the display with a variable force exerted by an energy storage member, and converting the variable force exerted by the energy storage member into a substantially constant force applied to the display with a balance mechanism. The balance mechanism includes a first cam, a second cam rotationally coupled to the first cam, and a wheel rotationally coupled to the first cam and the second cam, wherein the first cam and the second cam are configured to convert the variable force exerted by the energy storage member into a substantially constant force applied to the display.

These and various other features and advantages will be apparent from a reading of the following detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 3A and 3B are partial, exploded views of a bottom portion of the lift mechanism of FIG. 1 in accordance with an embodiment of the invention.

FIG. 7 is a side plan view of the cam member of FIG. 6A.

FIGS. 13A and 13B are rear perspective views of a positioning apparatus in a lowered position and a raised position, respectively, in accordance with an embodiment of the invention.

FIG. 14 is a perspective view of a portion of a balance mechanism in a state corresponding to a first position of a mounting portion.

FIGS. 19A-19D are perspective views of a height adjustable desk in accordance with an embodiment of the invention.

FIG. 22A is a cross-sectional view of a lift mechanism in accordance with an embodiment of the invention.

FIG. 22B is a cross-sectional view of a bottom portion of the lift mechanism of FIG. 22A in accordance with an embodiment of the invention.

FIG. 22C is a partial top view of the lift mechanism of FIG. 22A in accordance with an embodiment of the invention.

FIG. 23A is a side elevation view of a height adjustable desk in accordance with an embodiment of the invention.

FIG. 23B is a perspective view of the height adjustable desk of FIG. 23A.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Some embodiments of the invention generally provide a load balancing mechanism that can be used to balance a wide variety of loads. As just one example, some embodiments include a lift mechanism that incorporates a load balancing mechanism. Additional embodiments provide a load balancing mechanism within other types of positioning device providing movement through one or more variously oriented ranges of travel. Some embodiments of the invention generally provide apparatuses capable of positioning various equipment relative to a human operator. For example, in some cases a positioning apparatus including a load balance mechanism can support items such as electronic displays, a laptop computer (i.e., notebook), a keyboard, and/or other computing equipment, such as a mouse. As used herein, the term electronic display is used to refer to televisions, computer monitors, tablet computers, and other types of displays capable of displaying images from electronic signals. The embodiments discussed herein provide several examples of lift mechanisms and positioning apparatuses incorporating load balance mechanisms that are capable of positioning such types of computing equipment. However, it is contemplated that embodiments of the invention can be used for positioning a wide variety of items and the scope of the invention is not limited in this regard.

Figure 1:
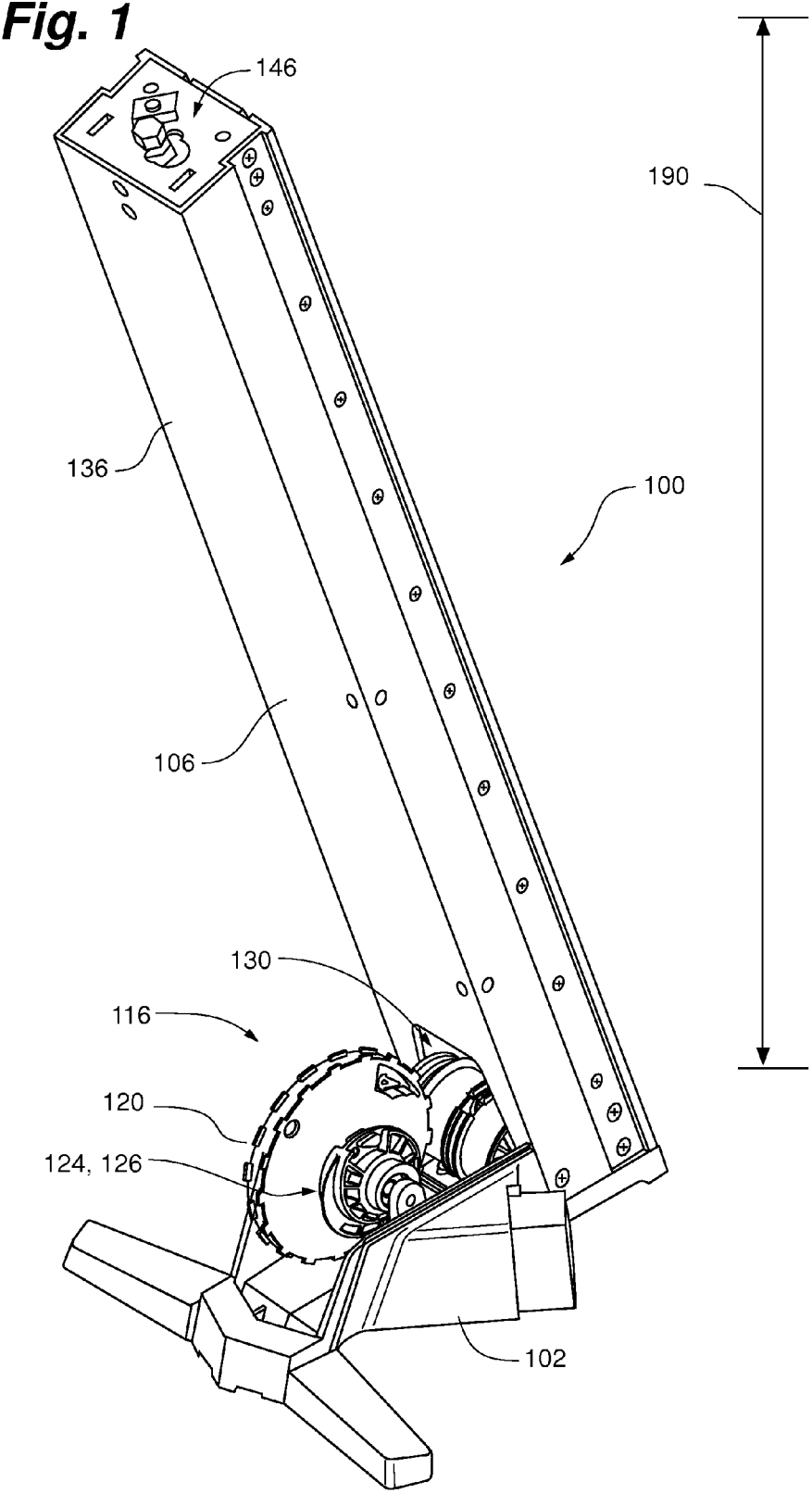
FIG. 1 is a perspective view of a lift mechanism in accordance with an embodiment of the invention.

FIG. 1 is a perspective view of a lift mechanism 100 incorporating a load balance mechanism 116 in accordance with an exemplary embodiment of the invention. The lift mechanism 100 can be useful for lifting a variety of loads, including electronic displays and/or computer-related equipment as will be discussed further herein. The lift mechanism 100 of FIG. 1 comprises a base 102 and a generally vertical support column 106 (sometimes referred to as a "riser") connected to the base 102. The base may include any structure for supporting the lift mechanism. In some embodiments, the base may include a relatively flat horizontal surface useful for placement on a horizontal work surface. In other embodiments, the base 102 includes a clamp to clamp the lift mechanism to a horizontal surface or a wall bracket to attach the lift mechanism 100 to a vertical wall. Portions of the balance mechanism 116 can also be seen in FIG. 1. As will be described in more detail herein, the portions of the balance mechanism shown in FIG. 1 include a wheel 120, a first cam 124, a second cam 126, and a pulley system 130.

Figure 12A:
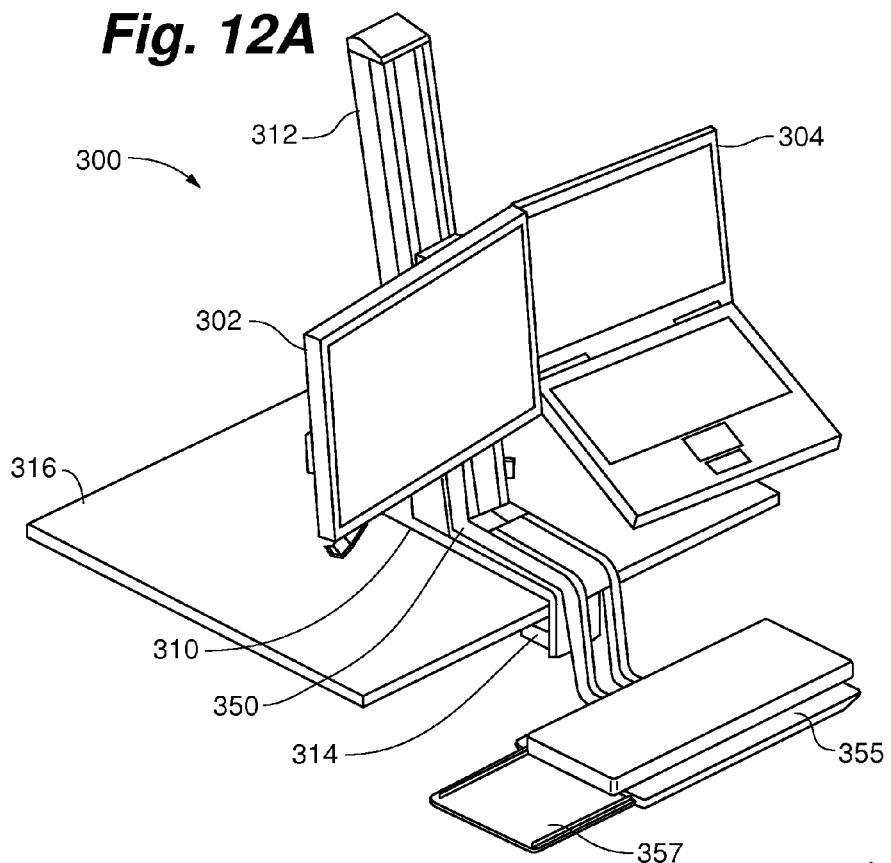
FIGS. 12A and 12B are front perspective views of a positioning apparatus in a lowered position and a raised position, respectively, in accordance with an embodiment of the invention.
Figure 12B:
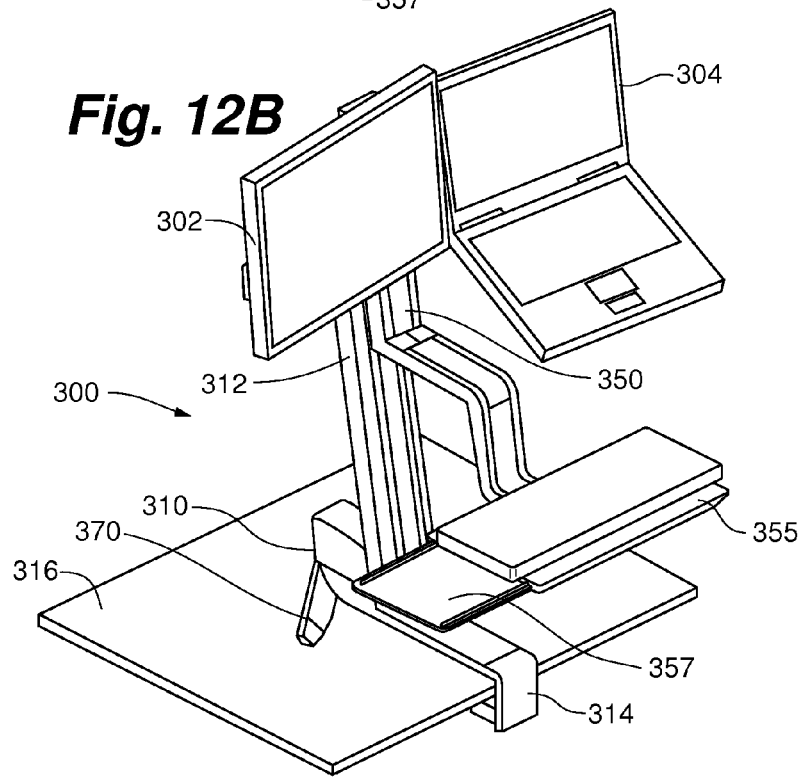

The support column 106 can be connected to the base by any suitable method. In some embodiments, the support column 106 is pivotably connected to the base such that the support column can pivot with respect to the base 102. In the embodiment shown in FIG. 1, the support column 106 is connected to the base 102 at an angle. The angle is useful for positioning the center of gravity of the monitor or other equipment carried by the support at a desired position with respect to the base to enhance stability. The support column 106 can be connected to the base 102 at any desired angle, including 90 degrees, less than 90 degrees, or more than 90 degrees. As shown in FIGS. 12A and 12B, the angle is somewhat more than 90 degrees.

Figure 2:
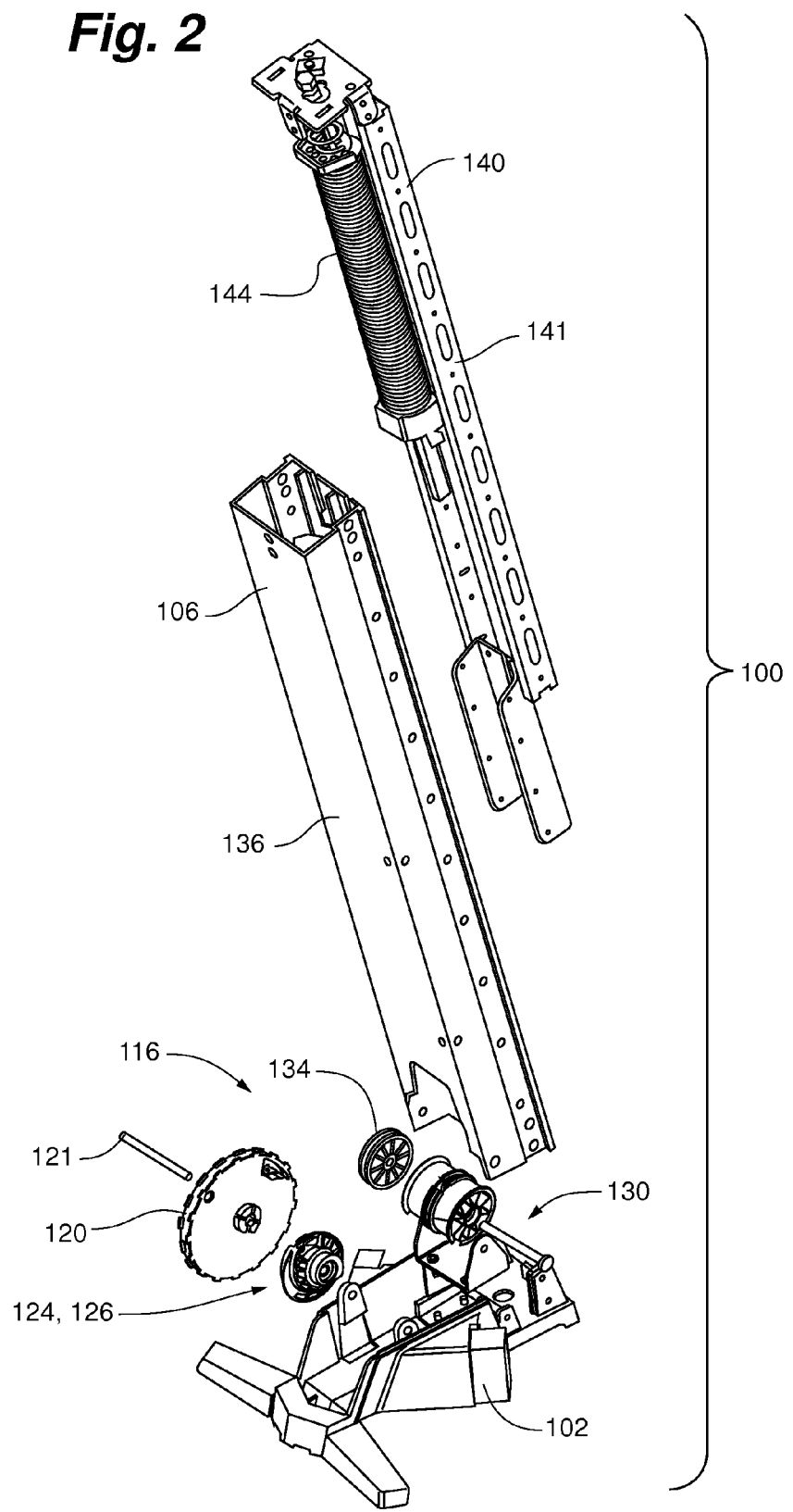
FIG. 2 is a partially exploded view of the lift mechanism of FIG. 1.
Figure 4:
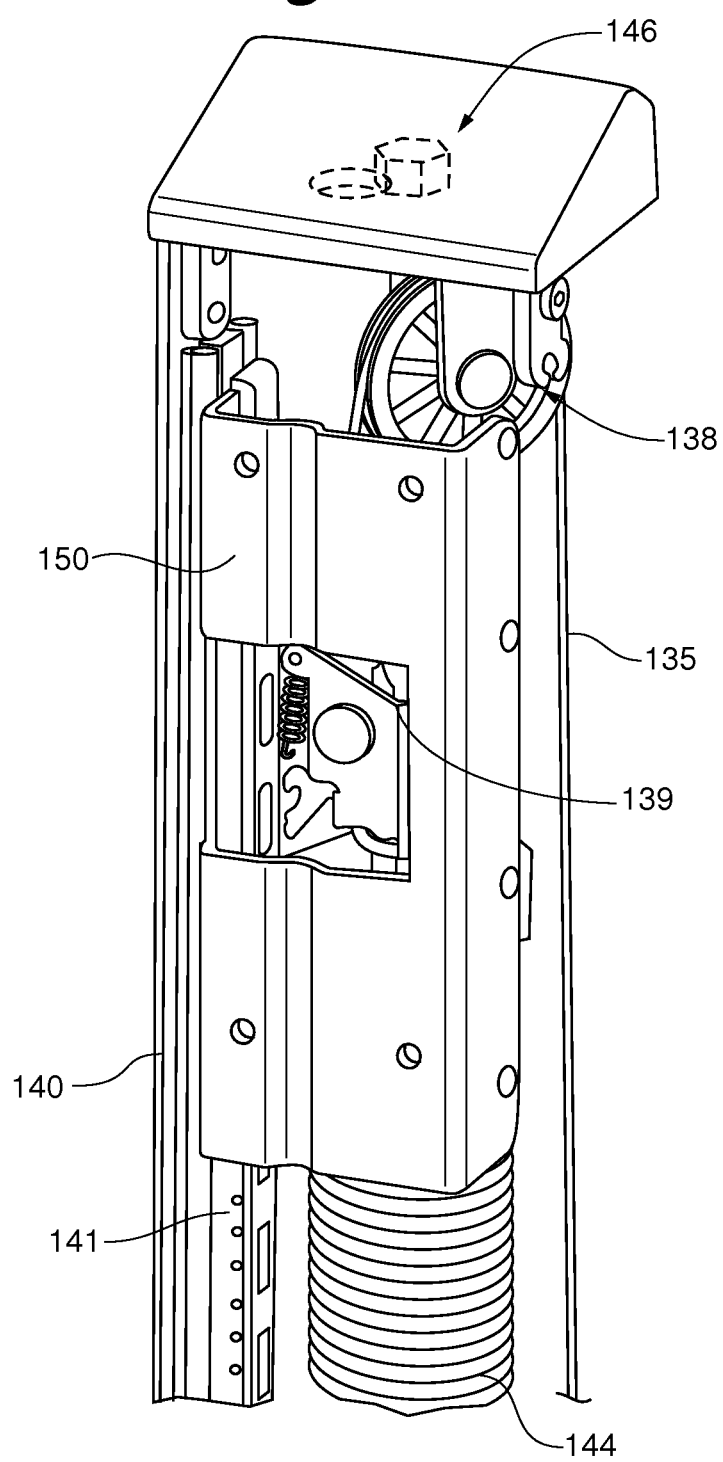
FIG. 4 is a partial elevation view of a top portion of the lift mechanism of FIG. 1 in accordance with an embodiment of the invention.

FIG. 2 is a partially exploded view of FIG. 1. In FIG. 2, it can be seen that the generally vertical support column 106 includes a first portion 136 and a second portion 140. As shown in FIG. 4, once fully assembled, a mounting portion 150 (e.g., sometimes referred to herein as a "truck") is coupled to the second portion 140. The mounting portion 150 and the second portion 140 are disposed in sliding engagement with one another such that the mounting portion can translate with respect to the second portion 140. For example, in some embodiments the second portion 140 includes a guide system, such as one or more rails 141 and the mounting portion 150 includes wheels or sliders that roll or slide along the rails. In general, the first portion 136 and second portion 140 are connected to base 102, and the mounting portion 150 can be connected to various types of equipment (e.g., one or more monitors and/or other computing equipment) that translate along with the mounting portion 150 with respect to the first and the second portions 136, 140. As shown in FIG. 2, an energy storage member 144 is coupled to the second portion 140. In this example the energy storage member 144 includes an extension spring, though it may optionally include any device useful for storing potential energy, including other types of springs (e.g., an extension spring, compression spring, torsion spring, etc.). In some embodiments the energy storage member 144 can be optionally adjustable via an energy storage member adjustment mechanism 146. In this example the adjustment mechanism 146 includes a threaded bolt with a bracket that changes the effective at-rest length of the energy storage member when actuated.

Returning to FIG. 1, the lift mechanism 100 provides a generally vertical range of travel 190 through which the mounting portion 150 (not shown in FIG. 1) can move. In some embodiments, the vertical range of travel 190 extends between a sitting height and a standing height, thus allowing an operator to use the lift mechanism 100 from both a sitting position and a standing position. For example, in certain embodiments the range of travel 190 is at least about 14 inches. In some embodiments the range of travel 190 is between about 14 inches and about 24 inches. The lift mechanism 100 in the positioning apparatus may also provide multiple positions at intermediate heights between the lowest and highest extents of the range of travel 190, thus accommodating other working positions and/or operators of different heights. In some cases a discrete number of intermediate positions are provided. In some cases the lift mechanism 100 provides an infinite number of intermediate positions within the vertical range of travel 190.

The balance mechanism 116 provides a balancing force between the first and second portions of the generally vertical support column 106 and the mounting portion 150, such that an operator can position equipment attached to the mounting portion at any desired height along the range of travel having only to overcome the friction of the system. Further, because of the balancing force provided by the balance mechanism, the mounting portion will hold its set position without the user having to engage any locks.

Figure 6A:
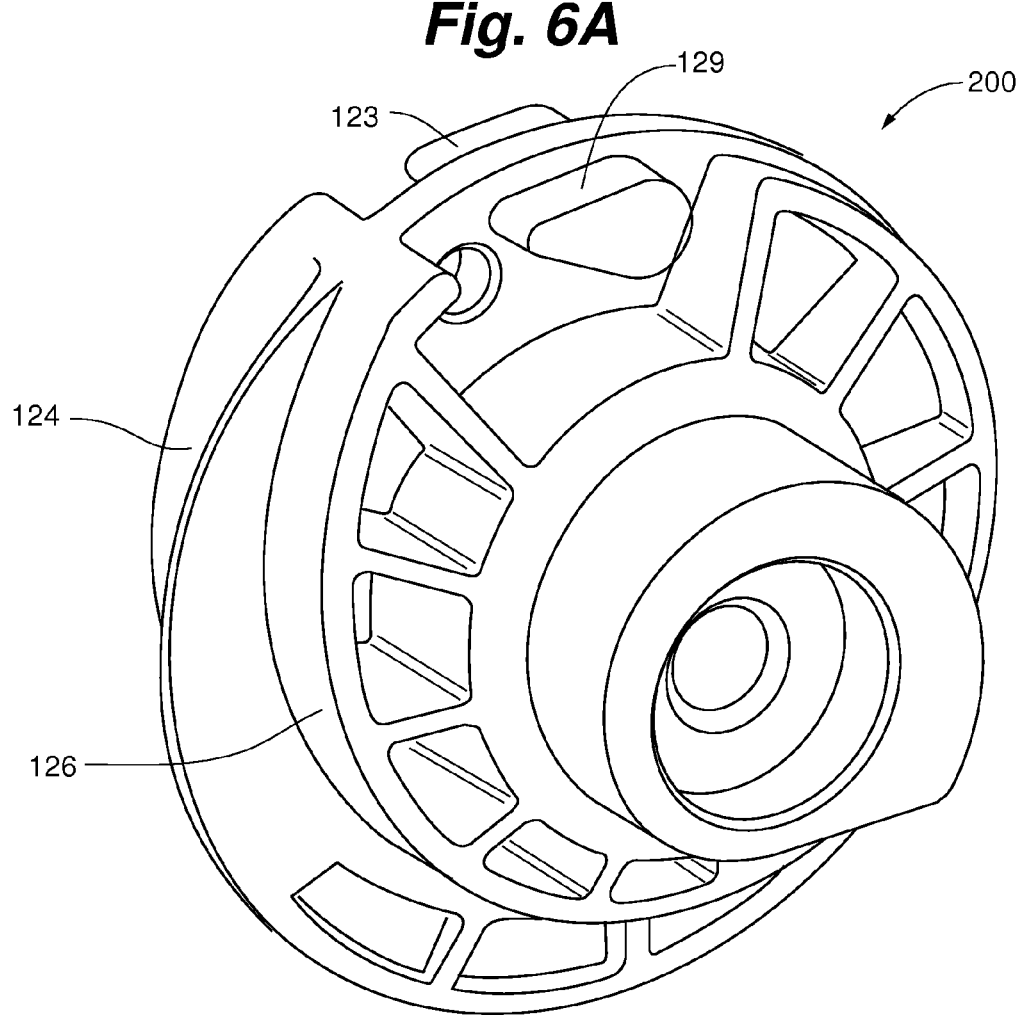
FIGS. 6A and 6B are perspective views of a cam member including a first cam and a second cam in accordance with an embodiment of the invention.
Figure 6B:
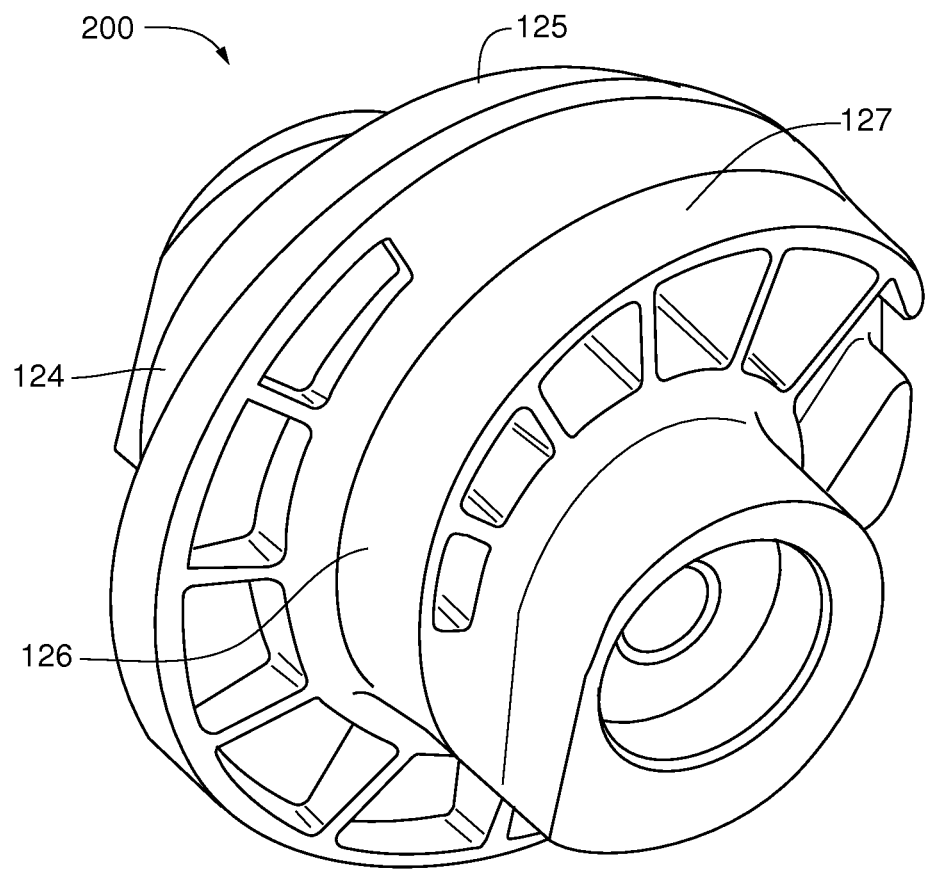
Figure 8:
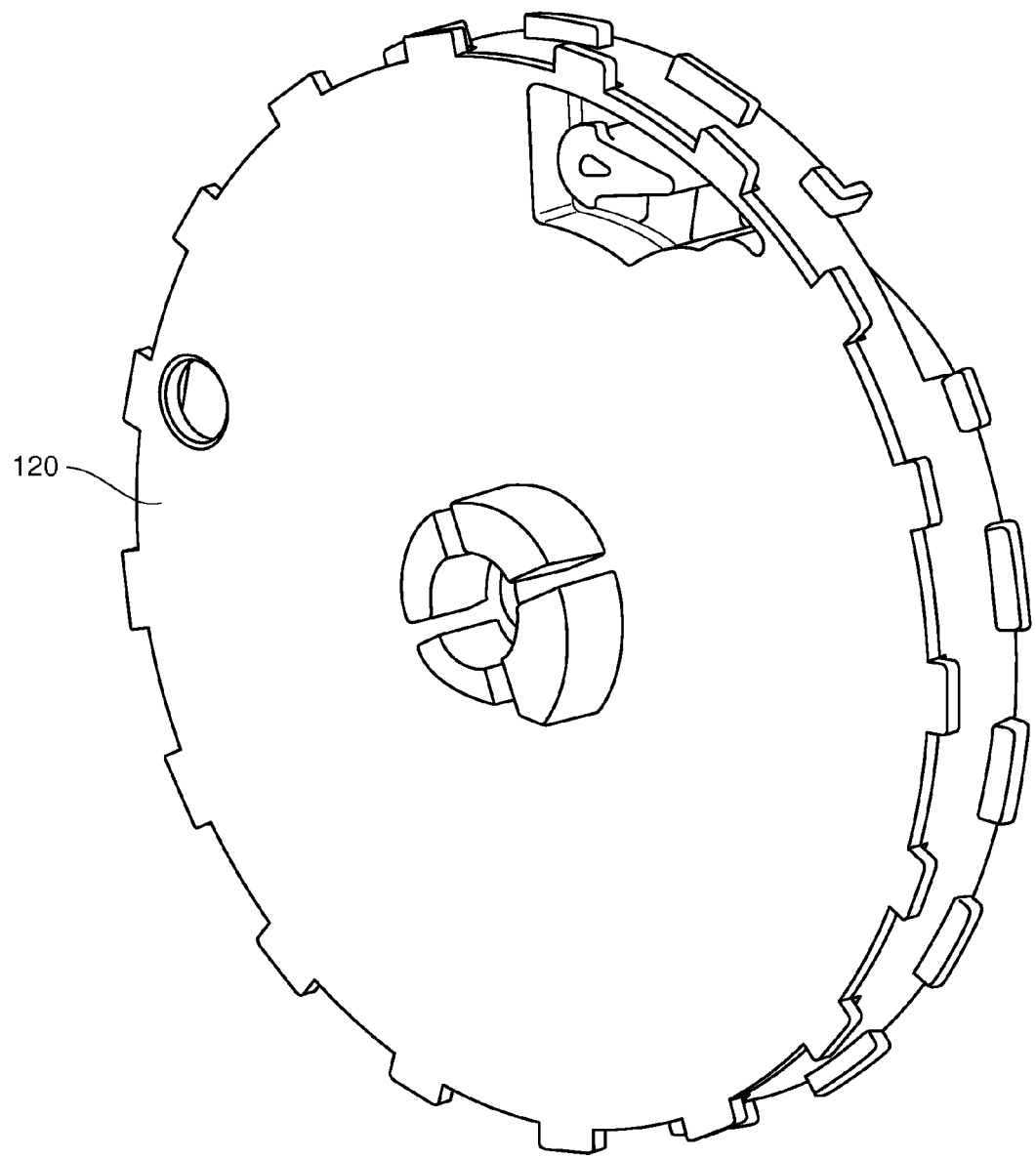
FIG. 8 is a perspective view of a wheel in accordance with an embodiment of the invention.
Figure 9:
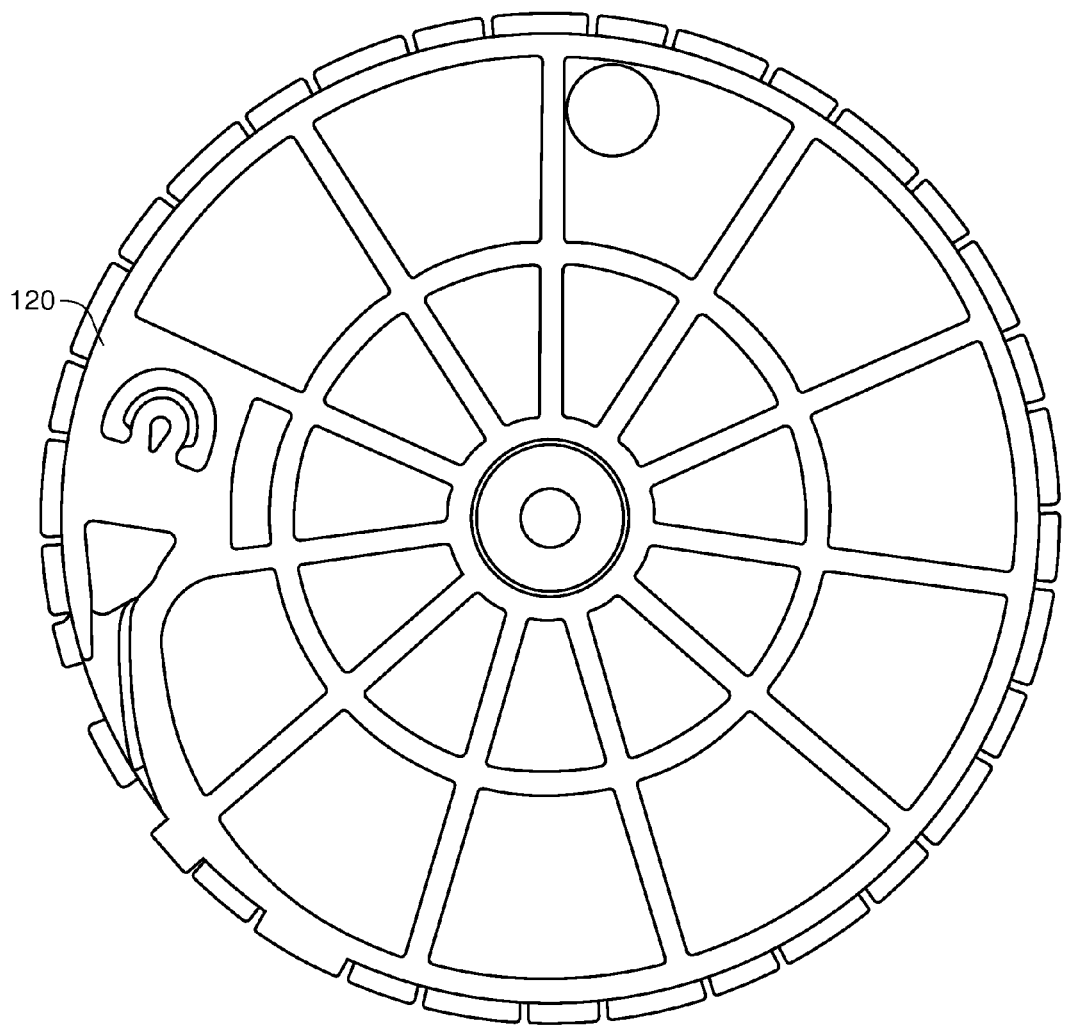
FIG. 9 is a side plan view of the wheel of FIG. 8.

In the embodiment of FIGS. 1 and 2, the wheel 120 is coupled to the first cam 124 and the second cam 126. The wheel 120 is rotationally fixed with respect to the cams such that the first and the second cams 124, 126 rotate along with rotation of the wheel. As shown, the first cam 124 and the second cam 126 can be provided as a single integral cam member. In addition, the wheel and cam member may be provided as different pieces connected directly together through axle 121. In other embodiments, they may be integrally formed and/or separated by a distance when installed. FIGS. 6A, 6B, and 7 provide perspective and side elevation views of a cam member including both the first and the second cams 124, 126 in accordance with an embodiment of the invention. FIGS. 8 and 9 provide perspective and side elevation views of the wheel 120 in accordance with an embodiment of the invention.

Figure 3B:
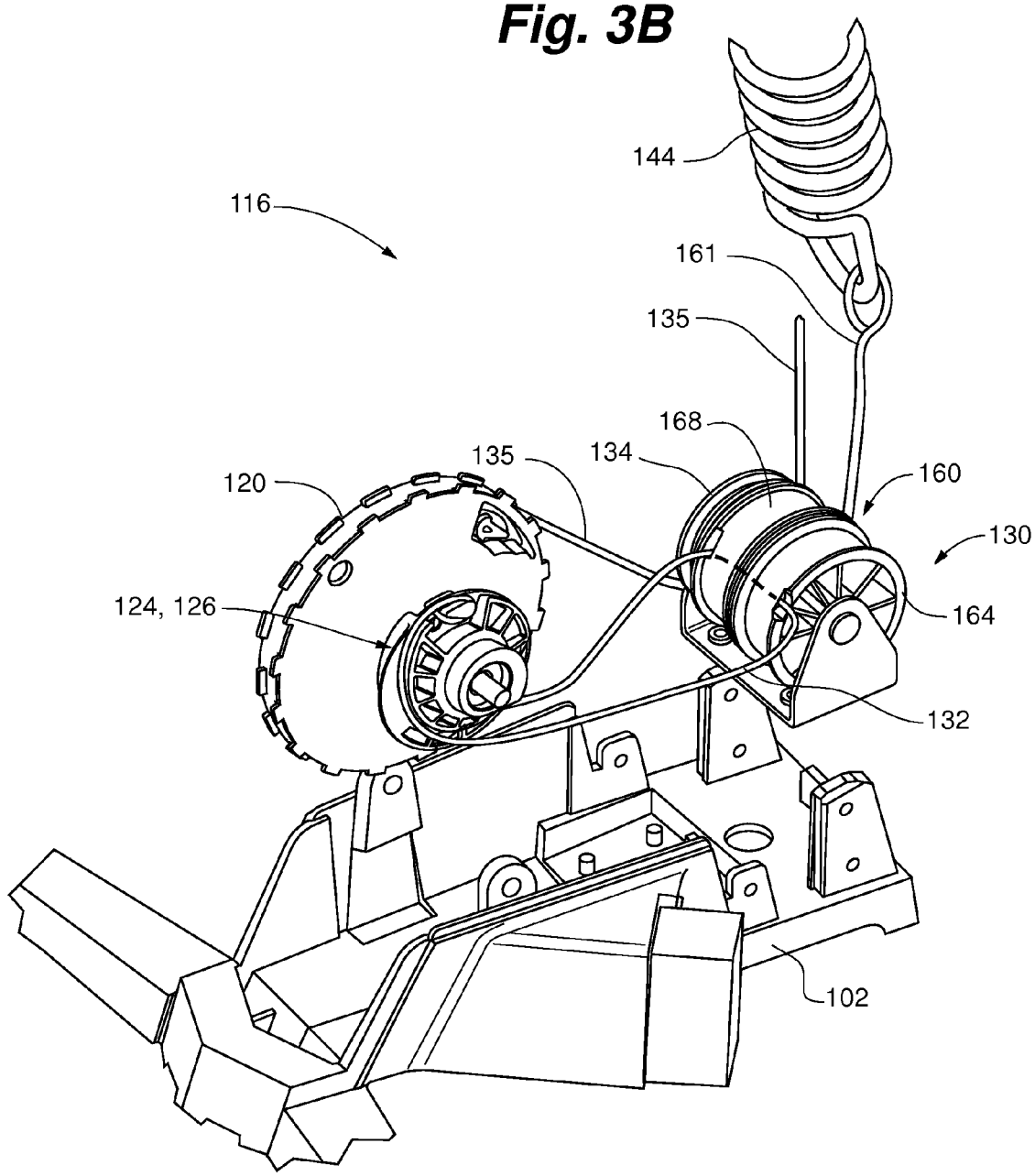

FIGS. 3A and 3B provide additional perspective views of the balance mechanism 116, illustrating an arrangement of the wheel 120, the first and the second cams 124, 126, a pulley system 130, and the energy storage member 144 in accordance with an embodiment of the invention. Although not shown, in some embodiments of the invention the first and the second cams 124, 126 are directly coupled to the energy storage member 144 via one or more flexible elements that are routed around pulley system 130. For example, two flexible elements could be attached to the end of the energy storage member 144, routed around the pulley system 130, and then coupled the cams 124, 126. The flexible element can be a rope or cable and can include any material useful for transmitting force, such as a tensile polymer.

Figure 10:
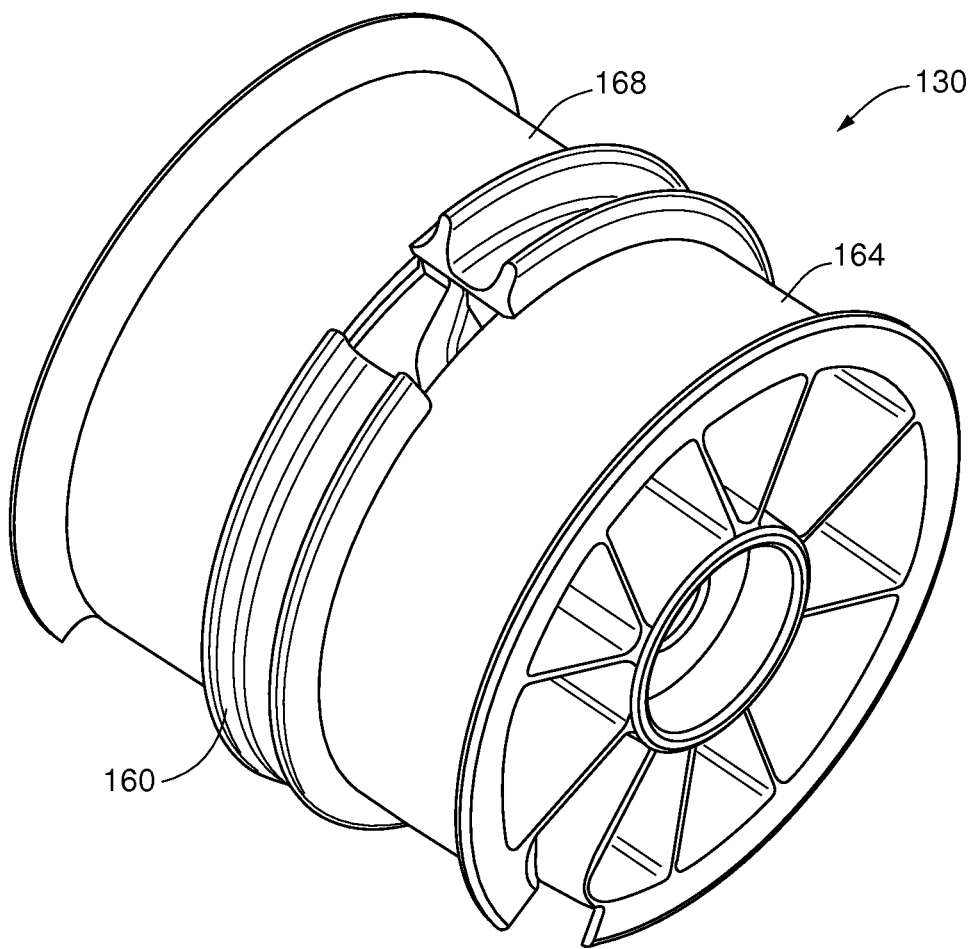
FIG. 10 is a perspective view of a pulley system in accordance with an embodiment of the invention.
Figure 11:
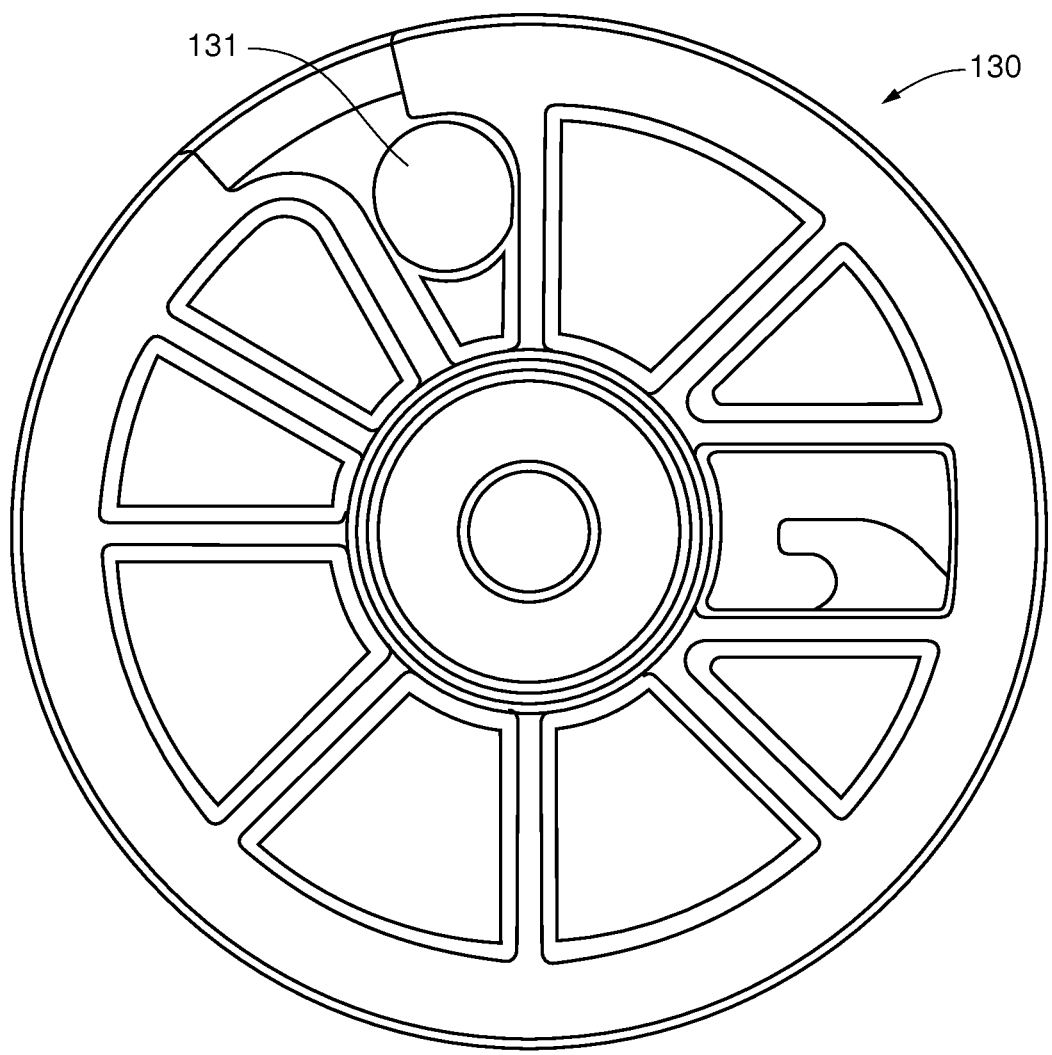
FIG. 11 is a side plan view of the pulley system of FIG. 10.

Referring to FIG. 3B, in some cases first cam 124 and second cam 126 are coupled indirectly to the energy storage member 144 via the pulley system 130. FIGS. 10 and 11 illustrate one embodiment of the pulley system 130, which includes first and second cam pulleys 164, 168, and an energy storage member pulley 160 coupled between the cam pulleys. As shown, in some embodiments the energy storage member pulley 160 and the cam pulleys 164, 168 are provided in a single piece construction though this is not required.

Referring to FIG. 11, in this embodiment the pulley system 130 includes a through hole 131, through which a single flexible element 132 can be threaded and then coupled to the cams 124, 126, one at each end. Such an arrangement is illustrated in FIG. 3B. As the cams rotate and pull (or loosen) flexible element 132, the flexible element 132 engages with the cam pulleys, and is unwound from (or wound around, respectively) each of the cam pulleys. An independent, separate flexible element 161 is coupled between the energy storage member 144 and the energy storage member pulley 160. The energy storage member pulley 160 rotates with the cam pulleys and thus winds and unwinds the flexible element 161 in order to engage the energy storage member 144.

Although not shown, in some embodiments each of the first and the second cams 124, 126 are optionally coupled to one of the cam pulleys 164, 168 with an independent, separate flexible element, while energy storage member pulley 160 is coupled to the energy storage member 144 via the separate flexible element 161.

Continuing with reference to FIG. 3B and 4, the wheel 120 is coupled to the mounting portion 150 coupled to the support column 106 with another flexible element 135. As the wheel 120 rotates with respect to the base 102, the mounting portion 150 moves with respect to the support column and vice versa. As shown in FIGS. 2 and 3B, an additional direction changing pulley 134 can direct the flexible element 135 between the wheel 120 and the mounting portion 150. Turning to FIG. 4, the direction of the flexible element 135 is again changed by an upper pulley 138 and the flexible element 135 is coupled to the mounting portion 150 using a hook 139 or another similar device known in the art.

Figure 5:
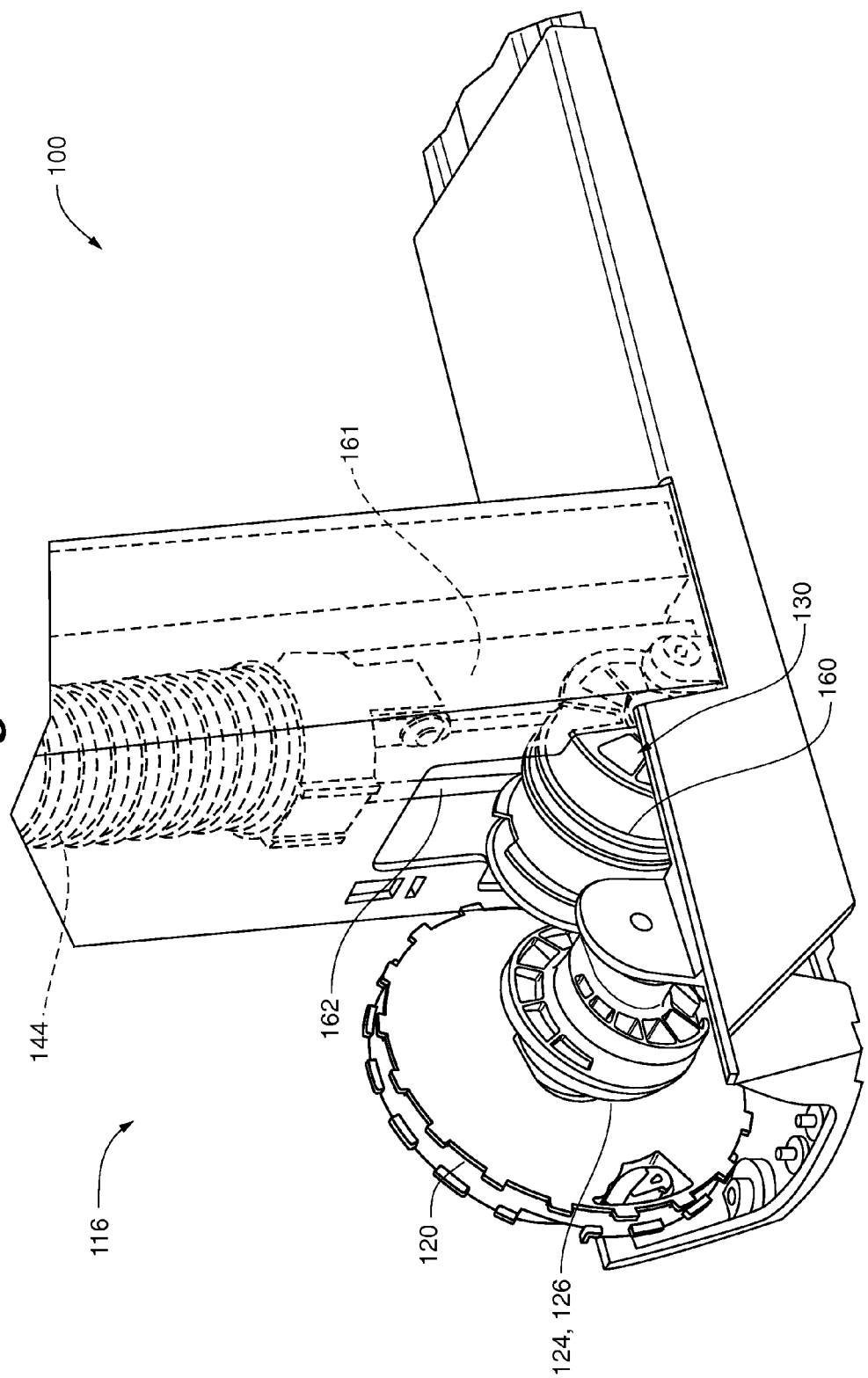
FIG. 5 is a perspective view of a bottom portion of the lift mechanism of FIG. 1 in accordance with an embodiment of the invention.

FIG. 5 is a partial perspective view of a bottom portion of the lift mechanism 100 having a slightly different base configuration than that shown in FIGS. 1-3B. As discussed above, the energy storage member pulley 160 is coupled to the energy storage member 144 via a separate flexible element 161. In some cases the energy storage member 144 includes a hook 162 that allows for easily coupling the flexible element 161 to member 144. In this embodiment, the energy storage member 144 is positioned within the support column 106 such that the hook 162 is generally aligned with the outer edge of the pulley system 130, and specifically with the outer edge of the energy storage member pulley 160. In some embodiments the energy storage member 144 and the pulley 160 may be positioned such that a longitudinal axis of the energy storage member is generally tangential to the edge of the pulley 160.

As the energy storage member pulley 160 rotates, it winds or unwinds the flexible element 161, allowing the energy storage member 144 to contract or causing the energy storage member to extend. Accordingly, the force or weight of the mounting portion 150, as well as any equipment coupled thereto, can be offset by the energy storage member 144, through the transmission and redirection of force through the flexible elements, pulleys, wheel and cams to the energy storage member 144.

FIGS. 6A and 6B provide perspective views, and FIG. 6C is a side view of a cam member 200 incorporating the first and the second cams 124, 126 according to some embodiments. As shown, the first cam 124 and the second cam 126 are incorporated into the single integral cam member 200, though this is not a requirement and the invention is not intended to be limited to this example. Some embodiments may have multiple separate cams that rotate together (e.g., rotationally synchronized about an axle), multiple cams integrated together into a single member, or a combination of both approaches. Returning to FIGS. 6A and 6B, the cams 124, 126 each include an attachment post 123, 129 for fixing the ends of the flexible element 132 to the cams as shown in FIG. 3B. The cams 124, 126 also each include a camming surface 125, 127 upon which each end of the flexible element 132 winds. According to some embodiments, the cam member 200 (or alternatively, the cams 124, 126 individually) can be formed from die cast, molded ABS plastic or nylon, or machined aluminum, among other suitable materials.

According to one example, as the energy storage member 144 (in this case an extension spring) contracts, it applies a linear force to the flexible element 161, which then applies a torque through the pulley system 130 and flexible element 132 to the cams 124, 126, thus urging rotation of the cams 124, 126 in a first direction. The torque applied by the energy storage member also urges rotation of the wheel 120 in the first direction since the wheel is rotationally clocked with the cams. As the wheel 120 rotates in the first direction, it winds the flexible element 135, thus pulling the mounting portion 150 (FIG. 4) up relative to the support column 106.

According to some embodiments, the energy storage member 144 does not exert a constant linear force on the flexible element 161. For example, an extension spring will exert a linear force that varies with the amount of extension or contraction of the spring. However, in some embodiments it is desirable to provide a relatively constant lifting force for the mounting portion 150, as a constant force tends to make adjustment of the lift mechanism easier and more ergonomically-friendly for operators. In some useful embodiments of the invention, the first and the second cams 124, 126 are cooperatively shaped and positioned to balance a force exerted on the wheel 120 by the mounting portion 150 with forces exerted by the energy storage member 144 on the cams 124, 126. For example, the cams may be shaped and positioned so that a varying torque applied to the cams by the flexible element 161 (via the varying linear force that the energy storage member exerts) is converted to a substantially constant torque applied to the wheel 120. The wheel 120 then relays the constant torque to the flexible element 135, creating a constant linear force for lifting the mounting portion 150 relative to the support column 106. The opposite effect takes place as the mounting portion 150 is lowered, with the balance mechanism 116 creating a substantially constant resistance against downward movement of the mounting portion.

In some embodiments, the effective radius of each cam 124, 126 varies as a function of the angular orientation of the wheel 120 in order to convert the varying torque to a constant torque. For example, the effective radius of each cam surface 125, 127 may decrease according to a predetermined force profile as each cam surface winds about the rotational axis of the cam member 200 between an outside (e.g., perimeter) of the cam and the axis. In some cases the force profile is a function of the displacement of the energy storage member 144. According to some embodiments, the two cams 124, 126 are mirror images of each other, and have the same profile of radius variation as a function of rotation. For example, the cams 124, 126 may be symmetrically formed about a plane that is perpendicular to the cam member's axis of rotation. However, this is just one example and is not required in all embodiments.

In some embodiments the first and the second cams 124, 126 are each designed to distribute approximately half of the lift force from the energy storage member 144 to the mounting portion 150 and any attached equipment. Referring to FIG. 3B, the pulley system 130, including the energy storage member pulley 160 and the two cam pulleys 164, 168, divide the force from the energy storage member 144 approximately in half. The cam pulley 164 then transmits about one half of the force to the second cam 126, and the cam pulley 168 transmits about one half of the force to the first cam 124. Although not shown, the same effect can also be achieved using separate flexible elements rather than the single flexible element 132, with the separate flexible elements either coupling the cams directly to the energy storage member 144, or indirectly through the pulley system 130.

Applicants have found that apportioning the force from the energy storage member 144 between the first cam and the second cam (or any desired number of cams) appears to decrease stress and fatigue on the flexible element 132, thus increasing the life of the balance mechanism 116 and lift mechanism 100 as will be discussed further herein. Reducing the amount of stress on the flexible element coupled to each cam also allows for a smaller radius of the cam, since the stress on the flexible element caused by the smaller radius is offset to some degree by the smaller force on each flexible element from the energy storage member 144. In addition, the ability to use a smaller radius for the cams in turn enables use of a smaller wheel 120. For example, in order to reduce the radius of the wheel 120 and still provide the same amount of linear travel for the mounting portion 150, the wheel 120 will need to rotate through more rotations. This will in turn cause more rotations of the cams 124, 126, which requires a smaller final cam radius in order to wind the flexible element 132 the same amount. Dividing the force from the energy storage member enables this reduction in radius. Accordingly, the size of the housing covering the balance mechanism 116 can be made smaller due to the smaller size of the wheel 120 and the cam member 200.

Figure 13A:
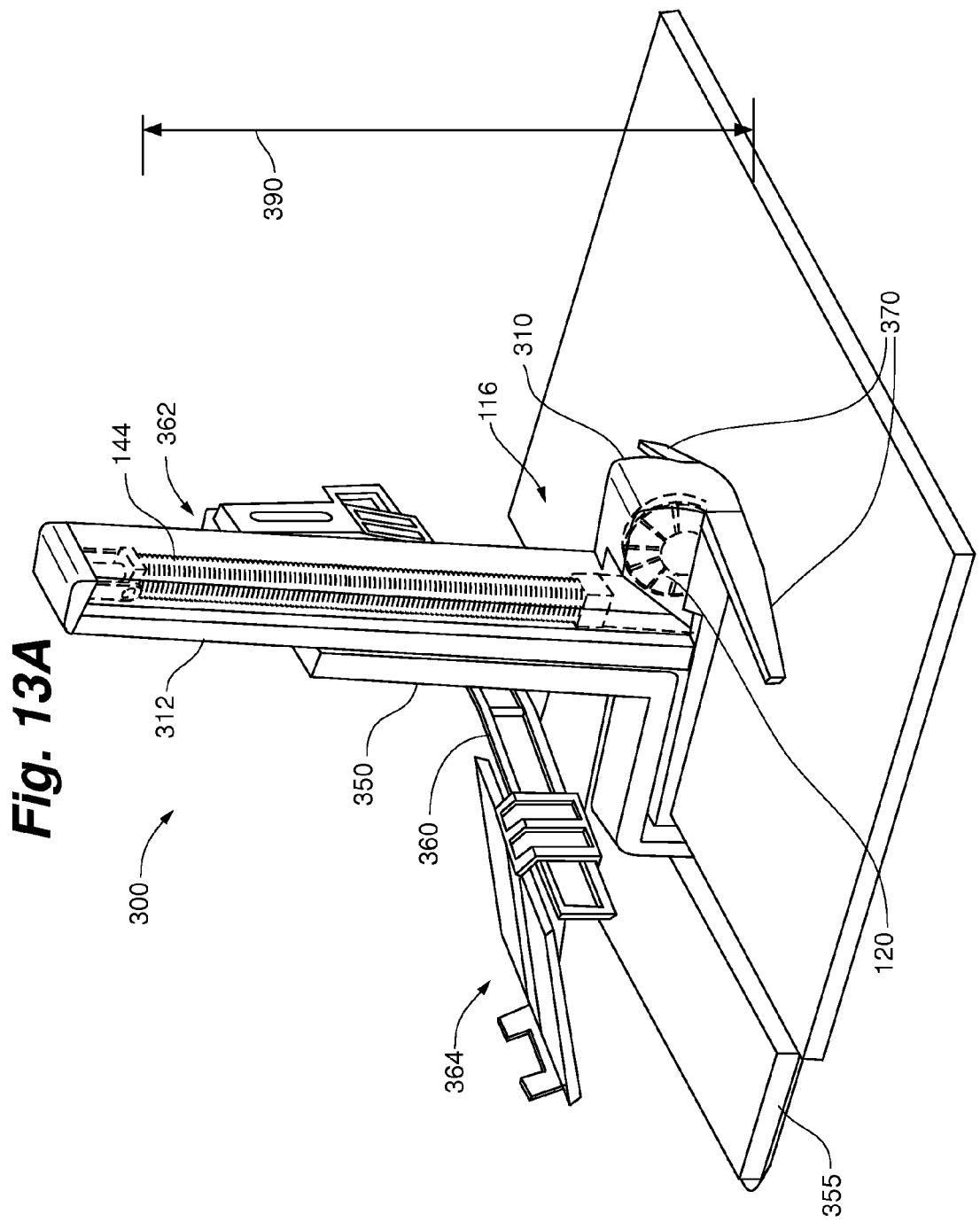

Some embodiments of the invention provide various types of balance mechanisms, lift mechanisms and positioning devices in different combinations according to embodiments of the invention. An example of a positioning apparatus 300 according to one embodiment of the invention will now be described with reference to FIGS. 12A-13B. FIGS. 12A and 12B show the positioning apparatus 300 in a lowered position and a raised position, respectively, from a front perspective. FIGS. 13A and 13B are rear perspective views of the positioning apparatus 300 in a lowered position and a raised position, respectively, without the supported display and notebook. Referring to FIGS. 12A-13B, the positioning apparatus 300 supports an electronic display in the form of a computer monitor 302, in addition to a notebook computer 304 in accordance with an embodiment of the invention. The positioning apparatus 300 includes a base 310 and a generally vertical support column 312 connected to the base 310. A movable mounting portion 350 is movably coupled to the support column 312 and attaches the monitor 302 and notebook 304 to the apparatus. In some cases the mounting portion 350 may also movably couple a keyboard tray 355 and a mouse tray 357 to the support column 312.

Referring to FIGS. 13A and 13B, the apparatus 300 includes a crossbar 360 attached to the mounting portion 350 for mounting various equipment. For example, in some cases a monitor mount 362 (e.g., a standard VESA connector), notebook tray 364, and/or other equipment mounts are attached to the crossbar 360, allowing the mounting portion 350 to support and move the monitor, notebook, and/or other equipment. It should be appreciated, however, that a wide variety of equipment can be moved by the mounting portion 350 and that the scope of the invention is not limited in this manner. For example, the mounting portion 350 may be configured to support and move a combination of one or more monitors and/or notebooks or other equipment. In some embodiments the mounting portion 350 is configured to support and move a combination of monitors and notebooks (e.g., two monitors and a notebook, three monitors and a notebook). In some embodiments the mounting portion 350 is configured to support and move multiple monitors, such as sets of two, three, or four or more monitors.

As shown in FIGS. 12A, 12B, 13A, and 13B, the positioning apparatus 300 can provide a wide range of travel 390 for the attached monitor and notebook. According to some embodiments, the height of the equipment (and mounting portion 350) can be set to any one of an infinite number of heights within the range of travel 390. FIGS. 12A and 13A illustrate positioning apparatus 300 in a low position (e.g., for sitting), while FIGS. 12B and 13B illustrate positioning apparatus 300 in a high position (e.g., for standing). To provide such adjustability for the monitor 302 and the notebook 304, positioning apparatus 300 in this embodiment includes the lift mechanism 100 and the balance mechanism 116 shown in FIGS. 1-11 and described above. FIGS. 13A and 13B illustrate the lift mechanism and the balance mechanism 116 incorporated into positioning apparatus 300. The wheel 120, as well as first and second cams 124, 126, and pulley system 130 (not shown) are positioned within the base 310. The energy storage member 144, in this case an extension spring, is positioned within the support column 312 and coupled between the support column 312 and the remaining portion of the balance mechanism.

According to some embodiments, the mounting portion 350 can itself provide some degree of adjustability between attached components. For example, as shown in FIGS. 12A, 12B, 13A, and 13B, in some cases a second lift mechanism is incorporated within or attached to the mounting portion 350. This can advantageously allow, for example, the crossbar 360, monitor 302 and the notebook 304 to be height adjusted with respect to the keyboard tray 355 to accommodate different users. The second lift mechanism can be any suitable mechanism known in the art. In some embodiments, the second lift mechanism includes a mechanism such as one of those taught in presently co-owned US Patent Application Publication US 2006/0185563 A1, which application was filed Sep. 28, 2005, the entire contents of which is incorporated by reference herein.

In the embodiment shown in FIGS. 12A and 12B, the support column 312 is connected to the base 310 at an angle, which is useful for positioning the center of gravity of the monitor 302 and notebook 304 at a desired location with respect to the base 310 to enhance stability. The support column 312 can be connected to the base at any desired angle, including 90 degrees, less than 90 degrees, or more than 90 degrees. As shown in FIGS. 12A and 12B, the angle is somewhat more than 90 degrees. According to some embodiments, the positioning apparatus 300 is advantageously configured to be used with an existing horizontal work surface 316, such as a desk or table. For example, base 310 may include multiple stabilizing legs 370 that hold the apparatus 300 upright on the work surface 316. In some cases base 310 includes a clamp 314 useful for securing positioning apparatus 300 to the horizontal work surface 316.

A positioning apparatus can include a base encompassing any structure that adequately supports the support column and the mounting portion upon a work surface. With continuing reference to FIGS. 12A-13B, according to some embodiments of the invention, the base 310 includes a first end and a second end with an elongated section extending between the first and the second ends. According to some embodiments, portions of the elongated section are formed with a low profile, thus minimizing any obstruction caused by the base and maximizing the range of travel of the mounting portion 350. In some cases the elongated section of the base 310 is generally parallel to the mounting portion 350.

In addition, in some cases the elongated section has a width approximately the same as a width of the mounting portion frame directly above the base and the support column 312. Such a configuration can advantageously reduce the footprint of the base 310 upon the work surface, thus leaving more room for other activities as well as reducing the visual impact of the positioning apparatus. For example, in some embodiments the widths of the elongated section of the base, the frame of the mounting portion, and the support column 312 are equal to or less than about 5 inches. In some cases, the widths of the elongated section, the frame of the mounting portion, and the support column 312 are equal to or less than a width of an electronic display mount (e.g., a VESA mount) attached to the mounting portion.

In some embodiments, the vertical range of travel 390 of the positioning apparatus 300 extends between a sitting height and a standing height, thus allowing an operator to use the apparatus 300 from both a sitting position and a standing position. For example, in certain embodiments the range of travel 390 is at least about 14 inches. In some embodiments the range of travel 390 is between about 14 inches and about 24 inches. The lift mechanism 100 in the positioning apparatus may also provide multiple positions at intermediate heights between the lowest and highest extents of the range of travel 390, thus accommodating other working positions and/or operators of different heights. In some cases a discrete number of intermediate positions are provided. In some cases the lift mechanism 100 provides an infinite number of intermediate positions within the vertical range of travel 390.

According to some embodiments of the invention, the positioning apparatus 300 is useful in applications in which a single operator may wish to both sit and stand while using the same monitor and/or notebook. For convenience, the positioning apparatus 300 can be described for such uses as a "sit-stand" positioning apparatus. Such sit-stand apparatuses can be useful in situations in which operators desire to perform operations in various postures, which may be required or desired to be performed at the same workstation. For example, one may desire to perform some operations in a seated position and other operations in a standing position. Certain embodiments of the invention provide a unique sit-stand positioning apparatus that is compatible with an existing, independent work surface (e.g., a desk top, table top, counter top, etc.) to form a sit-stand workstation. The positioning apparatus allows an operator to use the workstation at multiple heights if desired without the need for separate work surfaces at multiple heights. Accordingly, an operator does not need to move to a different workstation, but can adjust the height of the sit-stand workstation and continue using the existing workstation at the new height. Sit-stand positioning apparatuses may be subjected to more frequent adjustment (e.g., several times in a work day) than traditional, stationary monitor mounts, and embodiments incorporating multiple cam members as discussed above are thought to increase the cycle life of the apparatus as it encounters increased articulation. Further, some embodiments allow for relatively large ranges of travel while occupying a smaller footprint on a work surface where space is valuable.

Figure 15:
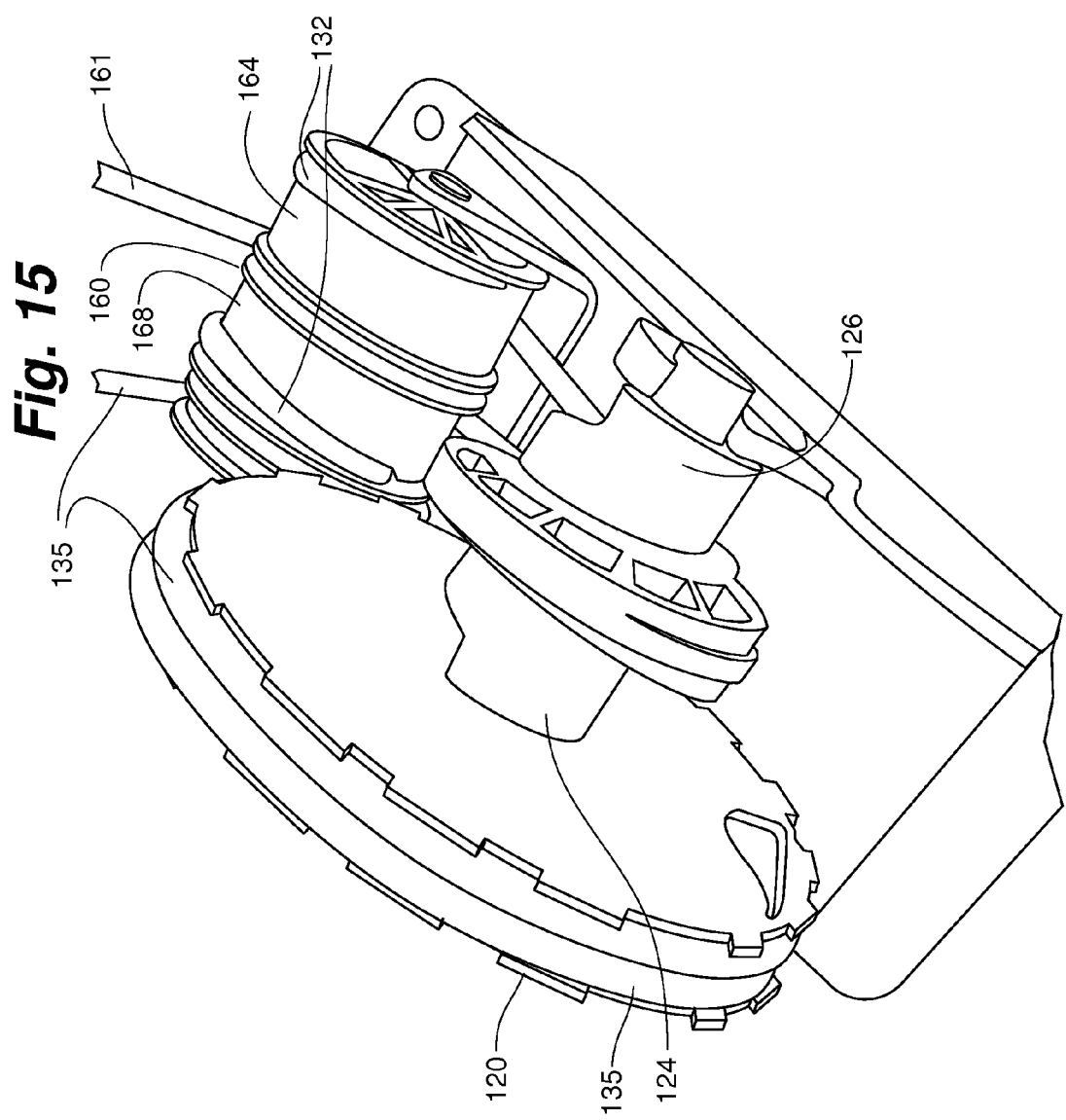
FIG. 15 is a perspective view of a portion of a balance mechanism in a state corresponding to a second position of a mounting portion.

In use, when an operator desires to change the position of a monitor or other device supported by the positioning apparatus 300, the operator can apply a force to the monitor and/or notebook. Movement of the monitor causes the mounting portion 350, to which it is attached, to also move relative to the support column 312 of the apparatus. FIG. 14 is a perspective view of a portion of the balance mechanism 116 in a state corresponding to the low position of mounting portion 350, while FIG. 15 is a perspective view of a portion of balance mechanism 116 in a state corresponding to the high position of mounting portion 350. As is shown, the mounting portion 350 is attached to the wheel 120 via flexible element 135, so that movement of the monitor/notebook causes the wheel 120 to turn about its axis. The first and second cams 124, 126, which are attached to the wheel 120, also rotate and cause the cam pulleys 164, 168 and energy storage member pulley 160 to rotate about their respective axes (which in this case are the same axis). Rotation of the energy storage member pulley 160 pulls or loosens flexible element 161, causing the energy storage member 144 to expand or allowing the member to contract in length. Since the shape of the cams 124, 126 are designed to accommodate a changing energy storage member force (e.g., based on spring length), the operator only need apply a relatively constant force to overcome friction to move the monitor to any desired position, and the monitor will stay in the desired position without having to lock it into that position.

Balance mechanisms including multiple cams as described above, and lift mechanisms and other types of positioning devices incorporating corresponding balance mechanisms, provide for surprising advantages over balance mechanisms that use a single cam. For example, balance mechanisms using multiple cams are more robust and reliable than single cam mechanisms. Applicants have surprisingly found that using a dual cam as described above can withstand a substantially greater number of cycles of adjustment compared to analogous single cam balance mechanisms. As just one example, Applicants have surprisingly found that increasing the number of cams within the balance mechanism by a factor of N can in some cases increase the load life of the mechanism by more than a factor of N. In some cases Applicants have found the load life to increase by a factor of 1.5N. In one case, Applicants surprisingly found that utilizing a balance mechanism including a dual cam as described herein increased the cycle life to 28,000 cycles from a cycle life of 10,000 cycles for a single cam mechanism under substantially similar conditions. Such an improved cycle life can increase the usefulness of practically any positioning apparatus, and provides an especially applicable and unexpected improvement for positioning apparatuses such as sit/stand positioning apparatuses that are subjected to a greater number of articulations than stands that are not able to accommodate a single operator in both sitting and standing postures.

Positioning apparatuses employing multiple cams also allow for heavier loads to be translated over a larger distance with a smaller cam housing size than analogous single cam balance mechanisms. This feature is particularly useful in positioning apparatuses that are designed to sit on top of a horizontal work surface and to accommodate an operator in both sitting and standing positions as they allow for relatively large ranges of travel while occupying a smaller footprint on a work surface where space is valuable. As one example, a positioning apparatus according to one embodiment includes a housing that accommodates a dual cam (e.g., first and second cams in FIGS. 1 and 2) that provides counterbalanced movement for an approximately 90 lbs. load over a distance of about 20 inches. In some cases this housing has an approximate size of 180 mm×125 mm×95 mm. In contrast, a housing for a single cam mechanism configured for a substantially similar load and distance can require a housing that is approximately 228 mm×203 mm×90 mm. Accordingly, such embodiments are useful for work surface top stands where space conservation is important. Of course the housing size may be smaller or larger, depending upon the particular weight and distance requirements for a particular apparatus. Some embodiments can be scaled to accommodate weights between about 3 lbs. and about 250 lbs. or more, and ranges of travel between about 2-3 inches up to 40 inches or more.

Without being bound by theory, Applicants believe that embodiments including multiple cams (e.g., a dual cam) provide advantages over single cam balance mechanisms because dividing the force of the attached equipment among two or more cams allows for a smaller force, and thus less stress, on each cam and associated flexible element, leading to an increased useful product life. In addition, each individual cam can be made smaller due to the smaller amount of load on each cam, while the full load can be carried by a single flexible element that wraps around the larger diameter of energy storage member pulley.

The following examples are presented to further illustrate embodiments of the multi-cam member (e.g., dual cam) described herein, and are not intended to limit the scope of the invention.

EXAMPLE 1

Comparable Example of Cycle Failure

Testing was carried out on a number of single cam balance mechanisms using an air cylinder with a 20" stroke. The single cam balance mechanisms each included a molded cam and other manufactured components including an extension spring and rope made according to specification to balance the desired weight over the desired range. The balance mechanisms were adjusted to a maximum weight to be balanced in order to apply the most stress to the rope. The air cylinder was connected to the moving component of the engine, and was cycled through its travel range at a rate of 6 cycles per minute. A targeted cycle life of 10,000 cycles under maximum loading was expected. In most cases, failure of the rope occurred at slightly more than 10,000 cycles but less than 12,500 cycles.

EXAMPLE 2

Cycle Failure of an Exemplary Dual Cam

Testing was carried out on a dual cam balance mechanism. Test set up, loading, cycle rate, rope material, weight range, and travel range were all identical to those in the testing of single cam mechanisms described in Example 1. Design differences included differences in cam design, spring design, and rope routing to accommodate the dual cam design. In at least one test of this configuration, the mechanism exceeded 28,000 cycles.

Figure 16A:
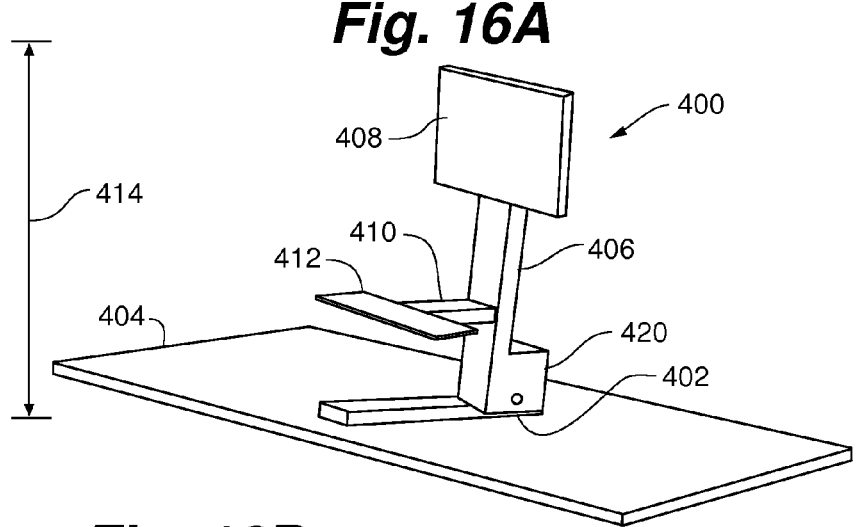
FIGS. 16A and 16B are front perspective views of a positioning apparatus in a raised position and a lowered position, respectively, in accordance with an embodiment of the invention.
Figure 16B:
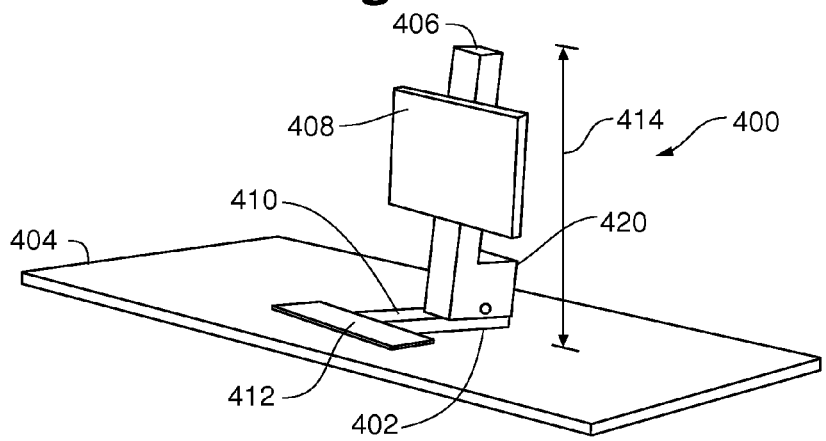

Turning to FIGS. 16A and 16B, another example of a positioning apparatus 400 according to some embodiments will be described. FIGS. 16A and 16B are schematic representations of front perspective views of a positioning apparatus 400 in a raised position and a lowered position, respectively, in accordance with an embodiment of the invention. The apparatus includes a base 402, which in this case is attached to a work surface 404 at a front end of the base. Although not shown, a support column 406 is movably coupled to a mounting portion with a lift mechanism and a balance mechanism (located in a housing 420 attached to the base 402), such as one of those described herein. The mounting portion (not shown) supports a display 408 attached to a display mount. The mounting portion also includes a keyboard arm 410 and a coupled keyboard tray 412. The mounting portion (again, not separately shown) is configured so that as the mounting portion moves up and down relative to the support column 406, the keyboard tray 412 and display 408 move up and down through a generally vertical range of travel 414. As shown in FIGS. 16A and 16B, the vertical range of travel of the keyboard tray 412 is entirely above the work surface 404 in this embodiment. The apparatus 400 thus provides a multi-position workstation that allows the keyboard tray 412 and the display 408 to be moved between two or more positions (e.g., heights) above the work surface 404. In some embodiments the positioning apparatus 400 also includes an attachment mechanism (e.g., a clamp) for removably or fixedly attaching the apparatus to the existing work surface 404. The attachment mechanism can provide an added amount of stability versus simply resting upon the work surface 404. However, an attachment mechanism is not required and in some cases the positioning apparatus may simply sit on the work surface 404.

Figure 17:
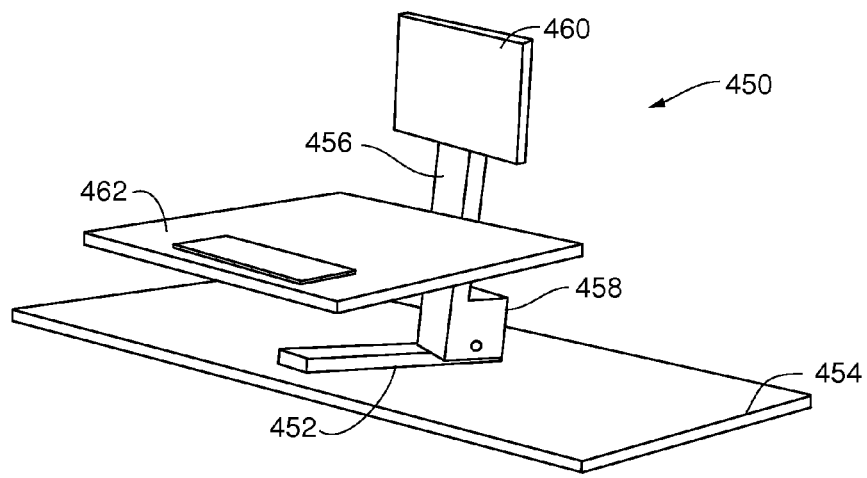
FIG. 17 is a perspective view of a positioning apparatus including a keyboard work surface in accordance with an embodiment of the invention.

FIG. 17 is a perspective, schematic illustration of another positioning apparatus 450 including a keyboard work surface 462 in accordance with an embodiment of the invention. The positioning apparatus 450 includes a base 452 attached to the work surface 454 at a front end of the base. Although not shown, a support column 456 is movably coupled to a mounting portion with a lift mechanism and a balance mechanism (located in a housing 458 attached to the base 452), such as one of those described herein. The mounting portion (not shown separately) also supports a display 460 attached to a display mount. The mounting portion also includes a movable work surface 462. The work surface 462 functions as a keyboard tray, but also provides a work area that can be useful to, e.g., read or mark up paper documents, support various items, etc. In some embodiments the positioning apparatus 450 also includes an attachment mechanism (e.g., either removably with a clamp, or fixedly with an adhesive or other fastener) for removably or fixedly attaching the apparatus to the existing work surface 454. The attachment mechanism can provide an added amount of stability versus simply resting upon the work surface 454. However, an attachment mechanism is not required and in some cases the positioning apparatus may simply sit on the work surface 454.

Figure 18A:
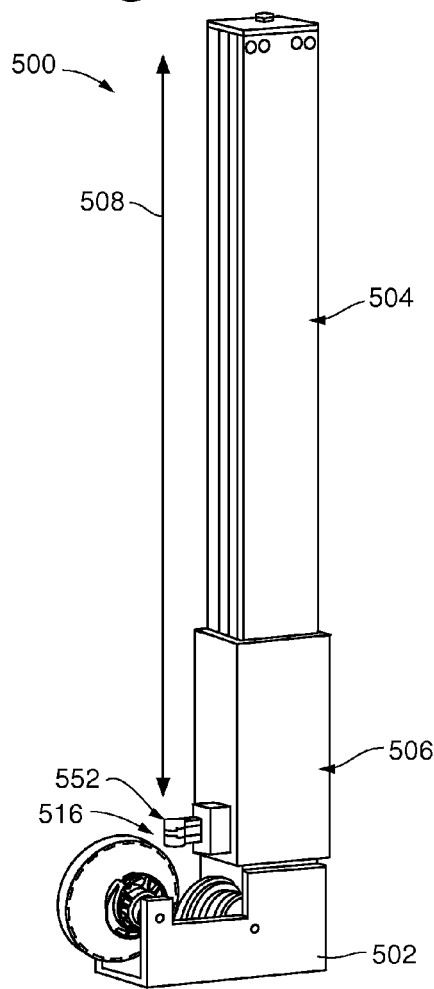
FIG. 18A is a perspective view of a lift mechanism in accordance with an embodiment of the invention.
Figure 18C:
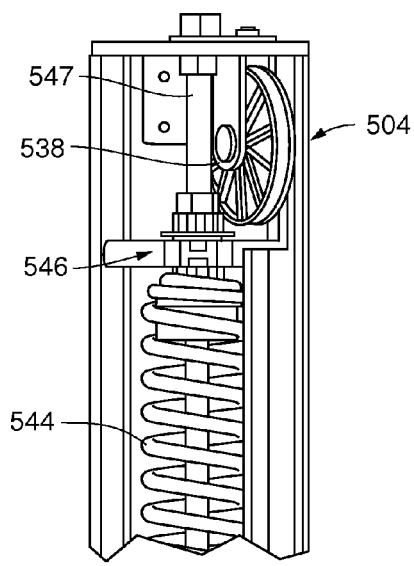
FIGS. 18B and 18C are cross-sectional views of a bottom portion and a top portion, respectively, of the lift mechanism of FIG. 18A.
Figure 18B:
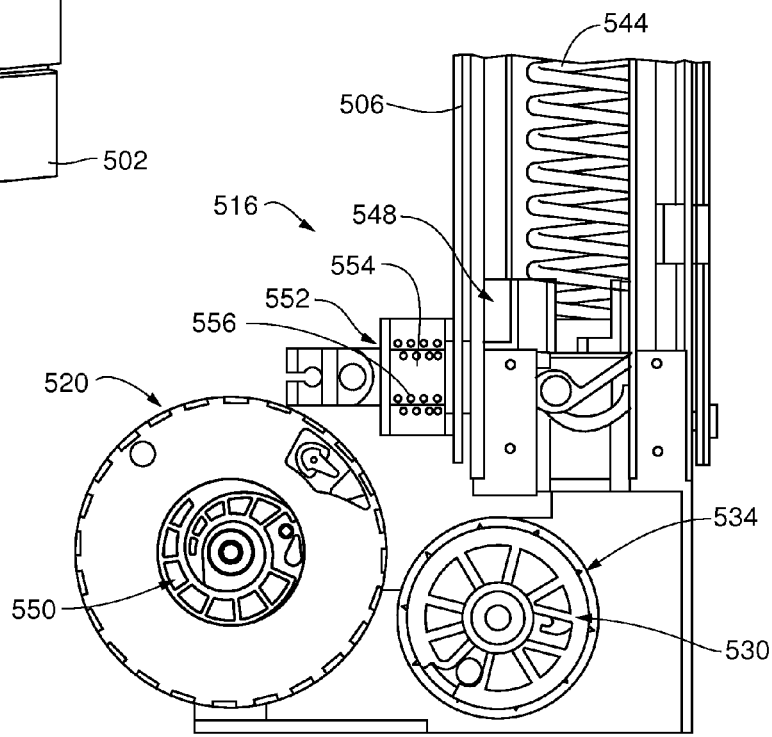

Turning to FIGS. 18A-18C, another example of a lift mechanism 500 is illustrated according to an embodiment of the invention. FIG. 18A is a perspective view of the lift mechanism 500, and FIGS. 18B and 18C are cross-sectional views of a bottom portion and a top portion, respectively, of the lift mechanism 500. The lift mechanism 500 includes a base 502 connected to a support column 504 (sometimes referred to as a "riser"). A mounting portion 506 is movably coupled to the support column 504 and configured to move up and down the support column 504 through a generally vertical range of travel 508. An energy storage member 544 is coupled to the mounting portion 506 for providing lift assistance. The lift mechanism includes an upper spring guide and attachment member 546 that attaches the energy storage member to the support column. The member 546 also guides adjustment of the tension of the energy storage member through an optional adjustment screw 547. A lower spring guide 548 is provided at the opposite end of the storage member to guide movement of the energy storage member as it extends and contracts. The lift mechanism 500 also includes a balance mechanism coupled between the mounting portion 506 and the energy storage member 544 for balancing forces between the energy storage member 544 and the mounting portion 506.

In this example, the lift mechanism 500 includes a balance mechanism 516 substantially similar to the balance mechanism 116 described above with respect to FIGS. 1-9. Turning to FIG. 18B, the balance mechanism 516 includes a wheel 520 that is rotationally coupled to a cam member 550 that includes two separate cams. A pulley system 530 includes dual cam pulleys that are coupled to the cams via flexible elements (not shown) and an energy storage member pulley coupled to the energy storage member 544 via another flexible element (not shown). As with the example in FIGS. 1-9, two direction-changing pulleys including a lower pulley 534 and an upper pulley 538 (see FIG. 18C) route another flexible element (not shown) between the mounting portion 506 and the wheel 520. Operation of the balance mechanism 516 occurs in a manner substantially similar to the example in FIGS. 1-9, with the cam member 550 converting a variable force from the energy storage member 544 into a substantially constant force for the mounting portion 506.

In the embodiment shown in FIGS. 18A-18C, the mounting portion 506 has a tubular construction with a rectangular cross-section that enables the mounting portion 506 to fit about the support column 504. The mounting portion 506 is movably coupled to the support column 504 with a guide system, including for example, rails within the support column and slides or rollers within the mounting portion. In some embodiments the tubular construction is symmetrical with respect to a longitudinal axis of the mounting portion, giving the mounting portion two pair of substantially identical opposing faces. The tubular construction and opposing faces provide multiple options for mounting equipment, thus enabling the same lift mechanism 500 to be used in a number of orientations and positions (e.g., left side and/or right side, front side and/or back side) without the need for a specially designed mounting portion for each possible position or orientation.

Referring to FIG. 18B, the lift mechanism 500 includes a brake mechanism 552 that is attached to the mounting portion 506 and engages the support column 504 to hold the mounting portion 506 at a desired position relative to the support column. The brake mechanism 552 includes a plunger 554 configured to fit within a set of slots in the support column 504. Although not shown, the slots can extend along the length of the support column, at least along the range of travel 508 for the mounting portion. A compression spring 556 urges the plunger 554 into the slots, thus providing a normally braked configuration at one of many vertical positions along the support column 504. According to some embodiments, the brake mechanism 552 can be temporarily disengaged by pulling the plunger 554 away from the support column, either directly or though the use of a cable and lever system.

FIGS. 19A-19D are perspective views of a height adjustable desk 600 incorporating the lift mechanism 500 shown in FIGS. 18A-18C in accordance with an embodiment of the invention. As used herein, a "height adjustable desk" and a "height adjustable table" may also be referred to as a display positioning apparatus in cases in which the desk/table is configured to support an electronic display. For example, an electronic display may simply rest upon a work surface of a desk or table, or the desk or table may include some other attachment mechanism for supporting a display.

The desk 600, which may also be referred to as a table, includes a base 602 supported by four feet 604. In some cases the feet 604 are height adjustable (e.g., with a threaded post) to provide for fine leveling of the desk's work surface. Alternatively, the base 602 could not include feet, or may optionally include casters. The base 602 is connected to a first lift mechanism 610 and a second lift mechanism 612, positioned on opposite sides of the base. As discussed above, the lift mechanisms 610, 612 each include a support column 614, a mounting portion 616, and a balance mechanism including multiple cams for balancing the forces exerted by the energy storage member and the load being carried. In this embodiment the balance mechanisms are provided in a covered housing 618.

The desk 600 further includes a work surface 620 having two side legs 622. The legs 622 are configured to attach to the mounting portions 616. In this embodiment the legs 622 comprise three sides that attach to three faces of the mounting portions 616. The three sides of the legs 622 form a longitudinal recess in the leg with a rectangular cross-section that fits about the support columns 614 and allows the legs to slide up and down about the support column. Of course, it should be appreciated that this is just one example of a possible configuration, and the legs 622 could be formed according to many other configurations that allow the legs to attach to the mounting portions 616. In addition, the legs 622 may be integrally formed with the work surface 620 as shown in the figures (e.g., as a molded plastic component), or may be separately formed and attached to the work surface 620.

The height adjustable desk 600 also includes some optional features, including cable management holes 630 in the work surface 620 and a braking system. The braking system includes the brake mechanism of each lift mechanism 610, 612 as described with respect to FIGS. 18A-18C, slots along the length of each support column, and a brake lever 640 positioned on the underside of the work surface 620. The brake lever 640 is coupled to the brake mechanisms with cables (not shown) routed through the legs 622 and attached to the plunger of each brake mechanism. Actuating the lever 640 pulls the plunger and disengages the brakes from each support column 614. Relaxing the lever 620 allows the plunger of each brake mechanism to reengage the support column due to the biasing force of the plunger spring. As shown in FIGS. 19A-19D, the support legs 622 include a brake housing 642 that accommodates and covers the brake mechanism in each lift mechanism.

While the brake system is useful for arresting movement of the desk 600, it may not be included in all embodiments of the invention. For example, in some cases the lift force from each lift mechanism 610, 612, as well as friction between the lift mechanisms' support columns and mounting portions will create sufficient force to offset the weight of the work surface 620 and maintain the desk's position. In addition, when used, the brake lever can be located in any suitable location relative to the desk 600, and may in some cases be proximate the base for foot actuation.

Referring to FIGS. 19A and 19B, in use the desk work surface 620 can be raised and lowered through a generally vertical range of travel 650 that provide multiple height positions for the work surface 620. FIG. 19 illustrates the adjustable desk 600 in a high position (e.g., for standing), while FIG. 19B illustrates the desk 600 in a low position (e.g., for sitting). In one embodiment, the vertical range of travel 650 extends between a sitting height and a standing height, thus allowing an operator to use the desk 600 at a sitting position and a standing position. For example, in certain embodiments the vertical range of travel 650 is at least about 14 inches. In some embodiments the vertical range of travel 650 is between about 14 inches and about 24 inches. The lift mechanisms 610, 612 in the desk 600 may also provide multiple positions at intermediate heights between the lowest and highest extents of the range of travel 650, thus accommodating other working positions and/or operators of different heights. In some cases a discrete number of intermediate positions are provided. In some cases the lift mechanisms provide an infinite number of intermediate positions within the vertical range of travel 650.

FIGS. 20A-20D illustrate another example of a lift mechanism 700 according to an embodiment of the invention. FIGS. 20E-20F illustrate a similar example of the lift mechanism 700 with the balance mechanism having a slightly different configuration from the configuration shown in FIGS. 20A-20D. In general, the lift mechanism 700 has a telescoping configuration, which can be useful for limiting the height of the lift mechanism in its lowest position. In addition, the telescoping action can enable attachment of the lift mechanism 700 to the underside of a surface, away from the edges of the surface (e.g., at the center of the surface).

Figure 20A:
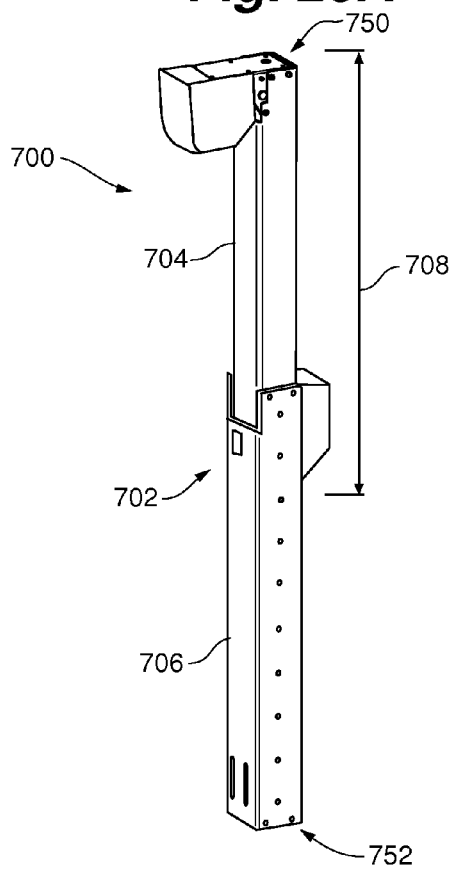
FIG. 20A is a perspective view of a lift mechanism in accordance with an embodiment of the invention.
Figure 20B:
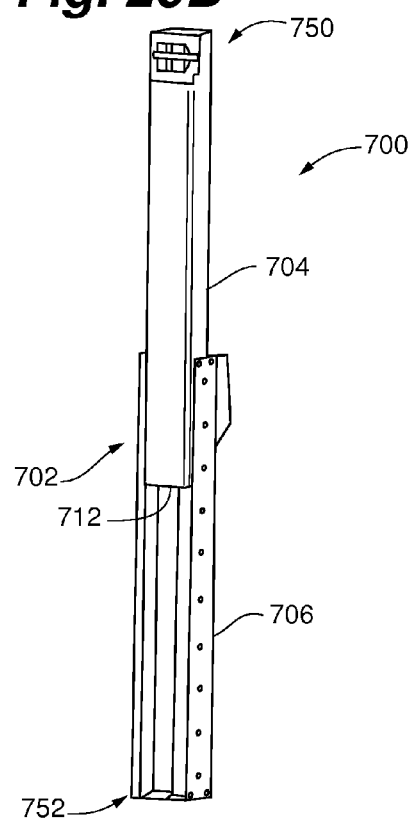
FIG. 20B is a partial sectional view of the lift mechanism of FIG. 20A.

FIG. 20A is a perspective view of the lift mechanism 700, while FIG. 20B is a partial sectional view of the lift mechanism 700. The lift mechanism 700 includes a riser 702 that is formed from an inner tube 704 and an outer tube 706. The inner tube 704 and the outer tube 706 are coupled in a sliding engagement with a guide system including, for example, rails and slides, glides, rollers, or any other suitable mechanism. As shown in FIGS. 20A-20B, the lift mechanism 700 is oriented such that the outer tube 706 can be attached to or rested upon a support surface and the inner tube 704 can be moved relative to the support surface and the outer tube 706. Accordingly, in some cases the outer tube 706 can be considered a support column and the inner tube can be considered a mounting portion. In certain embodiments, though, the lift mechanism 700 can be positioned in an opposite orientation such that the inner tube rests upon or is attached to a support surface and the outer tube 706 can be moved relative to the support surface and the inner tube 704. In such a case the outer tube 706 can be considered the mounting portion while the inner tube 704 acts as the support column.

In the embodiment shown in FIGS. 20A-20B, the inner and the outer tubes 704, 706 are slidingly engaged through a generally vertical range of travel 708. As the inner tube 704 slides out from the outer tube 706, the overall length of the lift mechanism 700 increases, while as the inner tube slides back into the outer tube, the length of the lift mechanism decreases. Accordingly, the length of the lift mechanism 700 adjusts as the inner tube 704 moves through the range of travel 708. The adjusting length is useful for reducing the height of the lift mechanism 700 when the lift mechanism is in a lower position. In addition, the lift mechanism does not require support column with a single, fixed length that accommodates the entire range of travel 708 at the same time.

Referring to FIGS. 20C-20F, the lift mechanism 700 includes an energy storage member 710 for providing lift assistance, which in this example comprises an extension spring. The energy storage member 710 is positioned within the inner tube 704 and attached at the lower end 712 of the inner tube, and thus moves up and down with the inner tube as the inner tube moves relative to the outer tube 706. An upper spring guide 714 is provided at the opposite end of the storage member to guide movement of the energy storage member as it extends and contracts. The lift mechanism 700 also includes a balance mechanism 716 coupled between the outer tube 706 and the energy storage member 710 for balancing forces between the energy storage member 710 and the outer tube 706. As discussed above, in some cases the lift mechanism 700 provides a discrete number of intermediate positions. In some cases the lift mechanism 700 provides an infinite number of intermediate positions within the vertical range of travel 708.

Figure 20C:
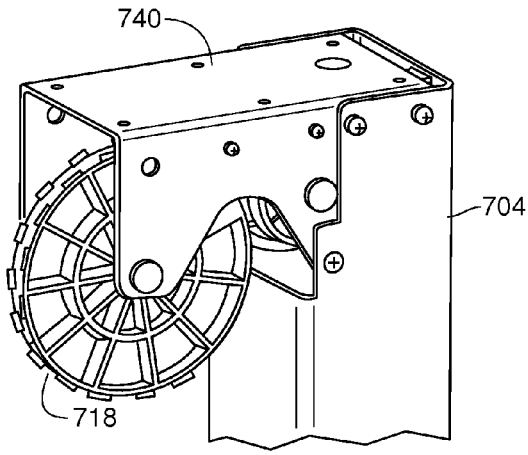
FIGS. 20C-20D are partial perspective views of a top portion of the lift mechanism of FIG. 20A.
Figure 20D:
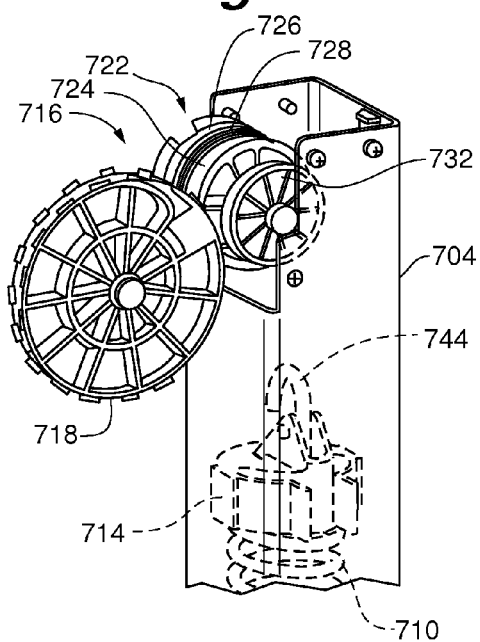
Figure 20E:
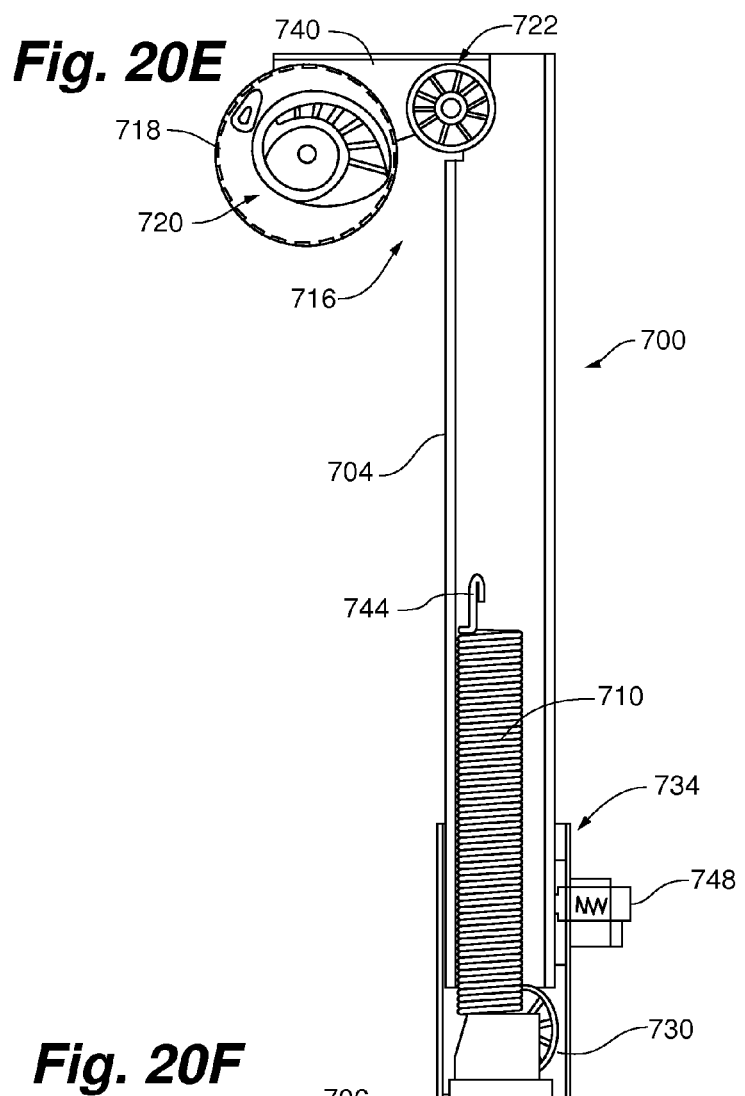
FIG. 20E is a cross sectional view of a lift mechanism in accordance with an embodiment of the invention.
Figure 20F:
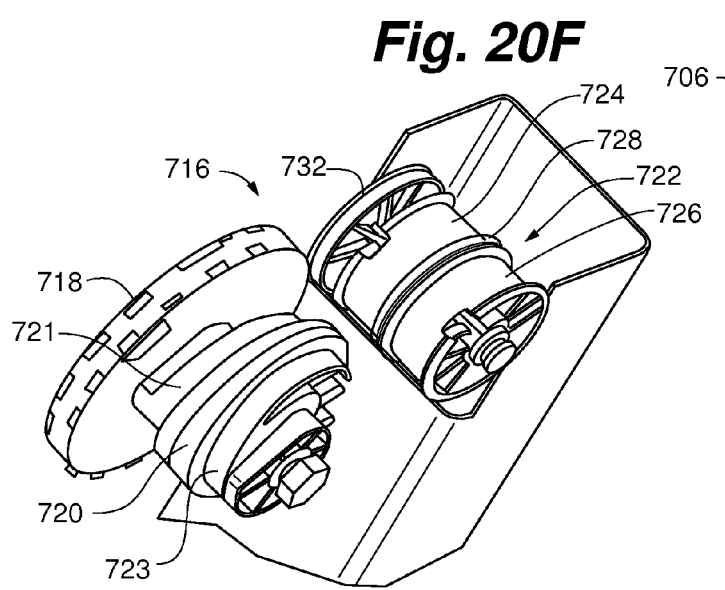
FIG. 20F is partial perspective view of a top portion of the lift mechanism of FIG. 20E.

In this example, the balance mechanism 716 is similar to the balance mechanism 116 described above with respect to FIGS. 1-9. The balance mechanism 716 includes a wheel 718 that is rotationally coupled to a cam member 720 (shown in FIGS. 20E-20F) that includes two separate cams 721, 723. A pulley system 722 includes dual cam pulleys 724, 726 that are coupled to the cams via flexible elements (not shown) and an energy storage member pulley 728 coupled to the energy storage member 710 via another flexible element (not shown). Two direction-changing pulleys including a lower pulley 730 and an upper pulley 732 route another flexible element (not shown) between the outer tube 706 and the wheel 718. FIGS. 20C-20D illustrate a first configuration in which the wheel 718, cam member 720, pulley system 722, and upper pulley 732 are mounted relative to the inner tube 704 with a bracket 740. FIGS. 20E-20F illustrate a similar configuration with the order of the wheel and cam member, and the pulley system and upper pulley reversed. In operation, the cam member 720 converts a variable force from the energy storage member 710 into a substantially constant force that lifts the inner tube 704 relative to the outer tube 706.

Although not shown in FIGS. 20C-20F, multiple flexible elements couple the parts of the balance mechanism 716 and the energy storage member 710. According to one example, a first flexible element is attached to the wheel 718 and routed over the upper pulley 732 down to the lower pulley 730. The first flexible element then wraps around the lower pulley 730 and is attached to an upper end 734 of the outer tube 706. Initially, when the lift mechanism 700 is in its highest position, the first flexible element is wrapped around the wheel 718. As the inner tube 704 moves down, the first flexible element pulls and rotates the wheel 718, thus uncoiling the first flexible element and allowing the down travel. In some cases the tension on the first flexible element is generally the same as the combined weight of the balance mechanism 716, the inner tube 704 and any equipment attached to the inner tube.

The wheel 718 is rotationally fixed with the cam member 720, and thus when the wheel 718 rotates, the cam member 720 also rotates. In this example a second flexible element (not shown) is routed from the each of the first and the second cams 721, 723 to the first and the second cam pulleys 724, 726 in a manner similar to the embodiment shown in FIG. 3B. Initially, the second flexible element is wrapped around the cam pulleys. As the wheel 718 and cam member 720 rotate, the first and second cams pull the second flexible element, which wraps around the cams 721, 723 and causes the cam pulleys to rotate. As discussed in the embodiments above, the use of the dual cams 721, 723 divides the tension of the lift mechanism among the cams.

The energy storage member 710 is located inside the inner tube 704 and attached to the lower end 712 of the inner tube. A third flexible element (not shown) connects the energy storage member pulley 728 with the upper end 744 of the energy storage member 710. As the cam pulleys 724, 726 rotate, the third flexible element wraps around the energy storage member pulley 728, thus pulling the upper end of the energy storage member 710 and creating an increasing spring force. The tension on the first flexible element (e.g., equal to the combined weight of the mounted equipment, inner tube, and balance mechanism) applies a substantially constant torque to the wheel 718. Each of the cams 721, 723 converts half of the increasing spring force (applied to each cam via the second flexible element) to a substantially constant torque equal to half of the torque carried by the wheel 718.

In some cases the energy storage member 710 is attached to the inner tube 704 in an adjustable manner to enable adjustment of the tension of the energy storage member depending on the weight that needs to be balanced. In this case, adjustment is achieved by controlling the position of the lower end of the spring via the adjustment mechanism. In some cases the adjustment mechanism can be based on a screw, warm gear, bevel gears, or other mechanism. Referring to FIG. 20E, in some cases the lift mechanism 700 includes a brake mechanism 748, which in this example is similar to the brake mechanism example as described with respect to FIGS. 18A-18C.

Turning to FIG. 20A, in some cases a work surface (or other equipment/items) can be mounted at the top end 750 of the inner tube 704 so that the balance mechanism 716 is attached to the work surface and positioned directly below the work surface. Some advantages of this configuration include freeing up space at the lower end 752 of the outer tube 706 that acts as the base of the lift mechanism 700 and somewhat concealing the balance mechanism with the work surface. While FIGS. 20A-20F illustrate this configuration, it is also possible that the lift mechanism 700 could be turned upside down and the work surface could be mounted to the "lower" end 752 of the outer tube 706 while the "upper" end 750 of the inner tube acts as the base of the lift mechanism.

Figure 21A:
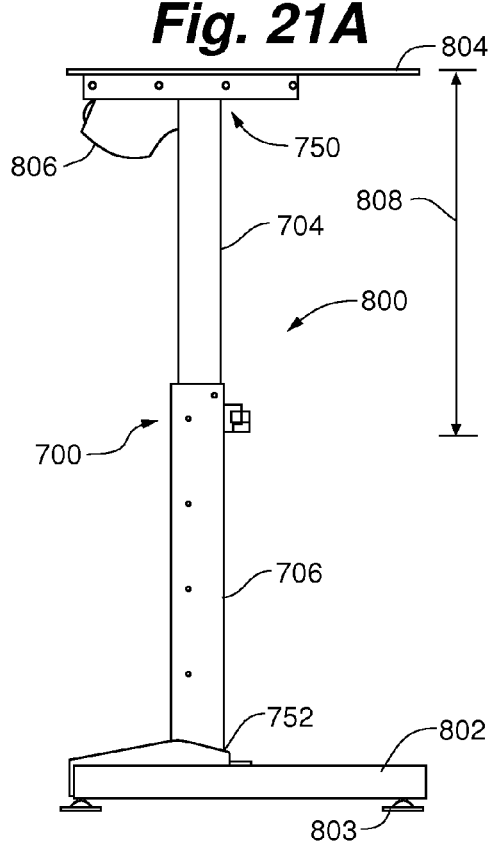
FIGS. 21A-21B are side elevation views of a height adjustable desk in accordance with an embodiment of the invention.
Figure 21B:
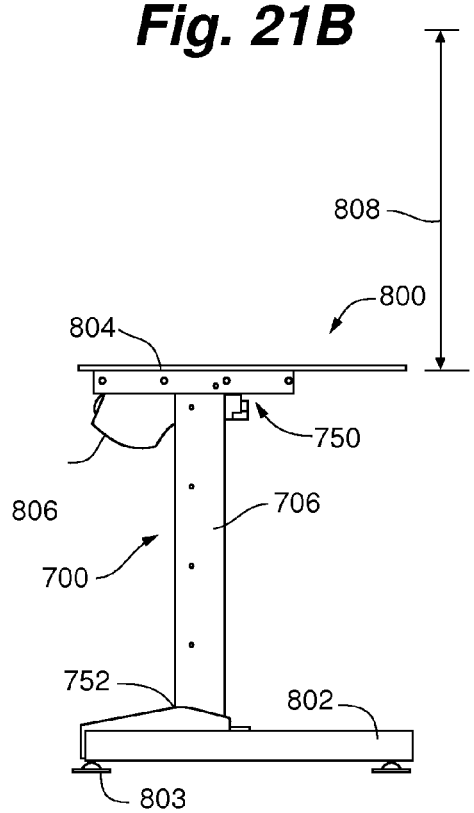

FIGS. 21A-21B and 21C-21D illustrate two examples of a height adjustable desk incorporating the lift mechanism 700 shown in FIGS. 20A-20F in accordance with embodiments of the invention. FIGS. 21A-21B are side elevation views of a stationary height adjustable desk 800 in accordance with an embodiment of the invention. The lift mechanism 700 is attached to a base 802 at the lower end 752 of the outer tube 706. In this embodiment the base 802 includes feet 803 for positioning the base on a floor or other surface. A work surface 804 is attached to the upper end 750 of the inner tube 704 and the balance mechanism 716 and a housing 806 surrounding the balance mechanism are located directly beneath the work surface 804. The height of the desk 800 is adjustable through a range of travel 808, including a high position (e.g., for standing) shown in FIG. 21A and a low position (e.g., for sitting) shown in FIG. 21B. As discussed above, in some cases the lift mechanism 700 provides a discrete number of intermediate positions. In some cases the lift mechanism 700 provides an infinite number of intermediate positions within the vertical range of travel 808.

As shown in FIGS. 21A-21B, use of the telescoping lift mechanism 700 allows the work surface 804 to be positioned (e.g., centered) on top of the lift mechanism, which can advantageously reduce any cantilevering between the work surface and the lift mechanism. Reducing cantilevering helps reduce friction in the guide system of the lift mechanism and lower the force needed by an operator to adjust the lift mechanism. In some cases this can enable the use of a single lift mechanism whereas multiple lift mechanisms may be necessary in other embodiments. For example, the embodiment described in FIGS. 19A-19D includes two lift mechanisms positioned near opposing edges of the work surface. In some embodiments, though, a single lift engine can be positioned near the edge of a work surface if sufficient structural features are present to respond to the cantilever load. For example, use of a longer truck and stronger support bracket under the work surface could allow a side mount configuration, although such features may increase costs.

Figure 21C:
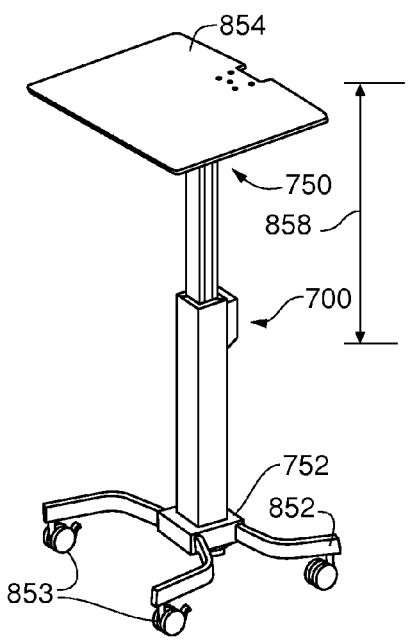
FIGS. 21C-21D are perspective views of a height adjustable desk in accordance with an embodiment of the invention.
Figure 21D:
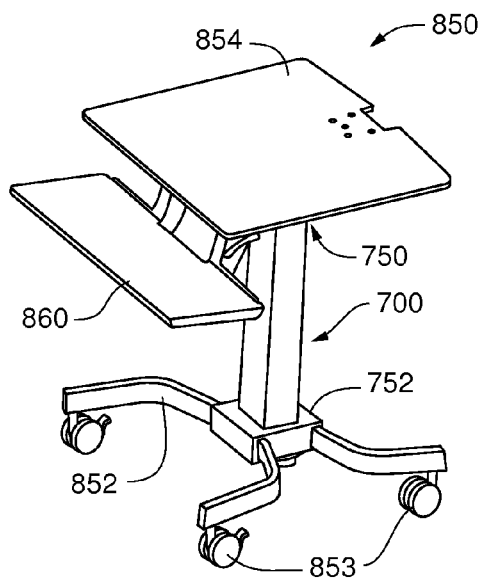

FIGS. 21C-21D are perspective views of a movable height adjustable desk 850 in accordance with an embodiment of the invention. The lift mechanism 700 is attached to a base 852 at the lower end 752 of the outer tube 706. In this embodiment the base 852 includes casters 853 that enable movement of the desk across a floor or other surface. A work surface 854 is attached to the upper end 750 of the inner tube 704 and the balance mechanism and a housing surrounding the balance mechanism are located directly beneath the work surface 854. The height of the desk 800 is adjustable through a range of travel 858, including a high position (e.g., for standing) shown in FIG. 21C and a low position (e.g., for sitting) shown in FIG. 21D. As discussed above, in some cases the lift mechanism 700 provides a discrete number of intermediate positions. In some cases the lift mechanism 700 provides an infinite number of intermediate positions within the vertical range of travel 858. FIG. 21D illustrates an optional keyboard tray 860 that may be attached to the work surface 854 in some embodiments.

Turning to FIGS. 22A-22C, another example of a lift mechanism 900 is illustrated according to an embodiment of the invention. FIG. 22A is a cross-sectional view of the lift mechanism 900, FIG. 22B is a cross-sectional view of a bottom portion of the lift mechanism 900, and FIG. 22C is a partial top view of the lift mechanism 900. The lift mechanism 500 includes a base 902 connected to a support column 904 (sometimes referred to as a "riser"). A mounting portion 906 is movably coupled to the support column 904 and configured to move up and down the support column 904 through a generally vertical range of travel 908. In this embodiment the mounting portion 906 comprises a three-sided bracket that rides along one side of the support column 904, although other configurations could also be used.

An energy storage member 944 is coupled to the mounting portion 906 for providing lift assistance. In this embodiment, the energy storage member 944 comprises a first extension spring 945 and a second extension spring 947. The lift mechanism includes an upper spring guide and attachment member 943 that attaches the energy storage member to the support column. The member 943 also guides adjustment of the tension of the energy storage member through an optional adjustment screw 946. Two lower spring guides 948 are provided at the opposite end of each of the first and second extension springs 945, 947 to guide movement of the springs as they extend and contract. The lift mechanism 900 also includes a balance mechanism coupled between the mounting portion 906 and the energy storage member 944 for balancing forces between the energy storage member 944 and the mounting portion 906.

In this example, the lift mechanism 900 includes a balance mechanism 916 similar to the balance mechanism 116 described above with respect to FIGS. 1-9. Turning to FIG. 22B and 22C, the balance mechanism 916 includes a wheel 920 that is rotationally coupled to a cam member 950 that includes a first cam 924 and a second cam 926. A pulley system 930 includes a first cam pulley 964 and a second cam pulley 968. The first cam pulley 964 routes a first flexible element 931 that is coupled at one end to the first cam 924 and at the other end to the first extension spring 945. The second cam pulley 968 routes a second flexible element 932 that is coupled at one end to the second cam 926 and at the other end to the second extension spring 947. A third flexible element 933 is coupled between the wheel 920 and the mounting portion 906. Two direction-changing pulleys including a lower pulley 934 and an upper pulley 938 (see FIG. 22A) route the third flexible element 933 between the mounting portion 906 and the wheel 920.

Operation of the balance mechanism 916 occurs in a manner similar to the example in FIGS. 1-9, with the cam member 950 converting a variable force from the energy storage member 944 into a substantially constant force for the mounting portion 906. However, in this embodiment the total lift force provided by the energy storage member 944 is provided by the two extension springs 945, 947 rather than a single extension spring shown in FIGS. 1-9. The use of the two extension springs reduces the necessary force provided by each spring (e.g., each spring can provide half of the lift force), which also reduces the force carried by each of the first and second flexible elements 931, 932. Also, since the necessary force is reduced, the extension springs 945, 947 can be formed from a smaller diameter wire and have a slightly smaller radius than would be required with a single extension spring (e.g., 5-10 mm smaller radius). Accordingly, when the springs are arranged side-by-side, the lift mechanism 900 can have a width that is narrower than would be necessary with a single spring. Aligning the support column 904 in about the same plane as the wheel 920 and cam member 950 thus provides a narrower configuration for the riser 900 that can provide more room for an operator in proximity to the riser 900.

FIGS. 23A-23B are views of a height adjustable desk 1000 incorporating the lift mechanism 900 shown in FIGS. 21A-21C in accordance with an embodiment of the invention. The lift mechanism 900 is attached to a base 1002 at a lower end of the support column 904. In this embodiment the base 1002 includes feet 1003 for positioning the base on a floor or other surface. The mounting portion 906 of the lift mechanism is attached to a work surface 1004 along one side of the work surface and the balance mechanism 916 and a housing 1006 surrounding the balance mechanism are located directly beneath the edge of the work surface 1004. The height of the desk 1000 is adjustable through a range of travel 1008, including a high position (e.g., for standing) shown in the figures and a low position (e.g., for sitting). As discussed above, in some cases the lift mechanism 900 provides a discrete number of intermediate positions. In some cases the lift mechanism 900 provides an infinite number of intermediate positions within the vertical range of travel 1008. An optional break mechanism 1020 can be included for stopping movement of the mounting portion 906 and the work surface 1004 as described above.

As shown in FIGS. 23B, the lift mechanism 700 near a back edge 1030 of the desk 1000 in this embodiment. The coupling of the lift mechanism near the back edge 1030 and the relatively narrow configuration of the riser 904 and balance mechanism housing 1006 combine to provide a greater amount of space underneath the work surface 1004 between the riser/balance mechanism and the front edge 1032 of the work surface 1004. Thus an operator can sit facing the front edge 1032 and have a greater amount of leg room below the work surface 1004.

Figure 24A:
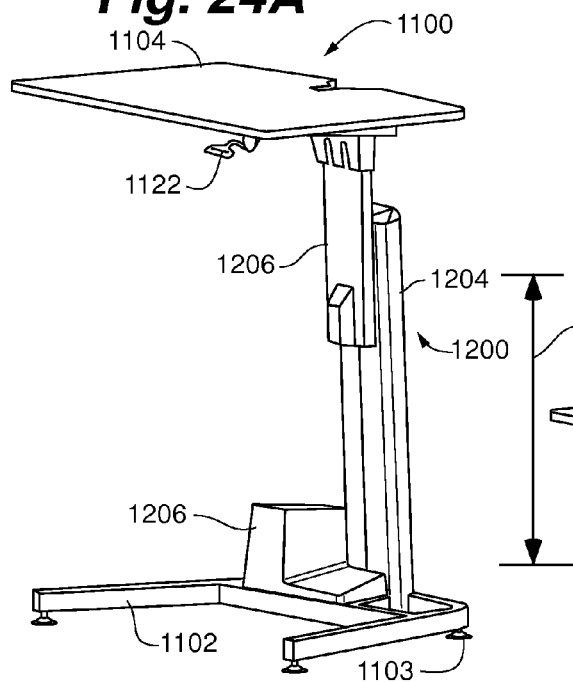
FIG. 24A is a perspective view of a height adjustable desk in accordance with an embodiment of the invention.
Figure 24B:
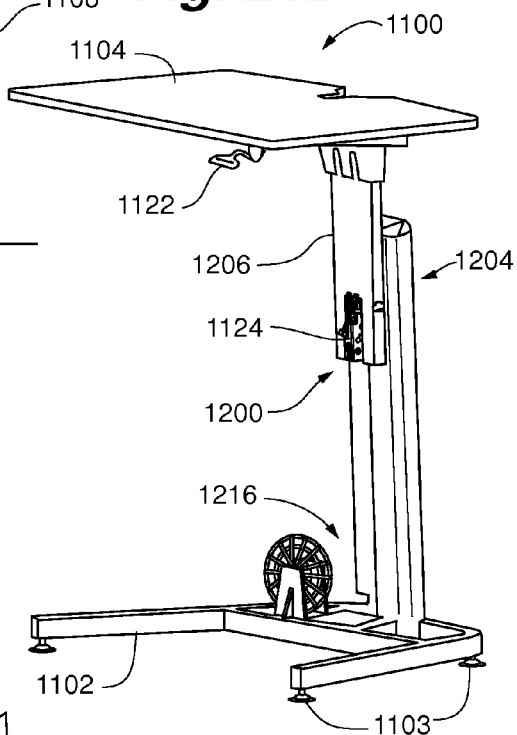
FIG. 24B is another perspective view of the height adjustable desk of FIG. 24A in accordance with an embodiment of the invention.
Figure 24C:
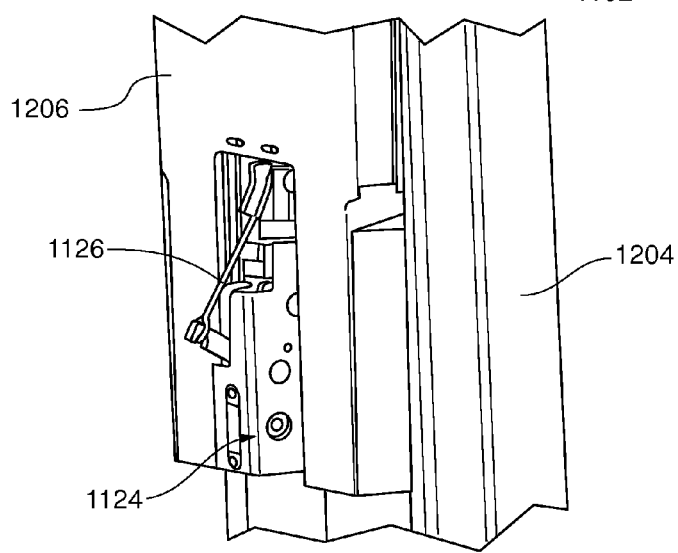
FIG. 24C is a partial perspective view of a brake mechanism of the height adjustable desk of FIG. 24A in accordance with an embodiment of the invention.

FIGS. 24A-24E illustrate a number of views of another height adjustable desk 1100 according to an embodiment of the invention that is similar in some respects to the desk 1000 shown in FIGS. 23A-23B. FIGS. 24A-24B are perspective views of the height adjustable desk 1100 incorporating a lift mechanism 1200 shown in more detail in FIGS. 24D-24E in accordance with an embodiment of the invention. The lift mechanism 1200 is attached to a base 1102 at a lower end of the support column 1204. In this embodiment the base 1102 includes feet 1103 for positioning the base on a floor or other surface. The mounting portion 1206 is attached to a work surface 1104 along one side of the work surface and the balance mechanism 1216 and a housing 1208 surrounding the balance mechanism are located directly beneath the edge of the work surface 1104. The height of the desk 1100 is adjustable through a range of travel 1108, including a high position (e.g., for standing) shown in the figures and a low position (e.g., for sitting). As discussed above, in some cases the lift mechanism 1200 provides a discrete number of intermediate positions. In some cases the lift mechanism 1200 provides an infinite number of intermediate positions within the vertical range of travel 1108. An optional break system including a brake lever 1122 and a brake mechanism 1124 can be included for stopping movement of the mounting portion 1206 and the work surface 1104 as described above. Turning to FIG. 24C, a cable 1126 can be routed through the lift mechanism between the lever 1122 and the break mechanism 1124 for actuating the break mechanism.

Figure 24D:
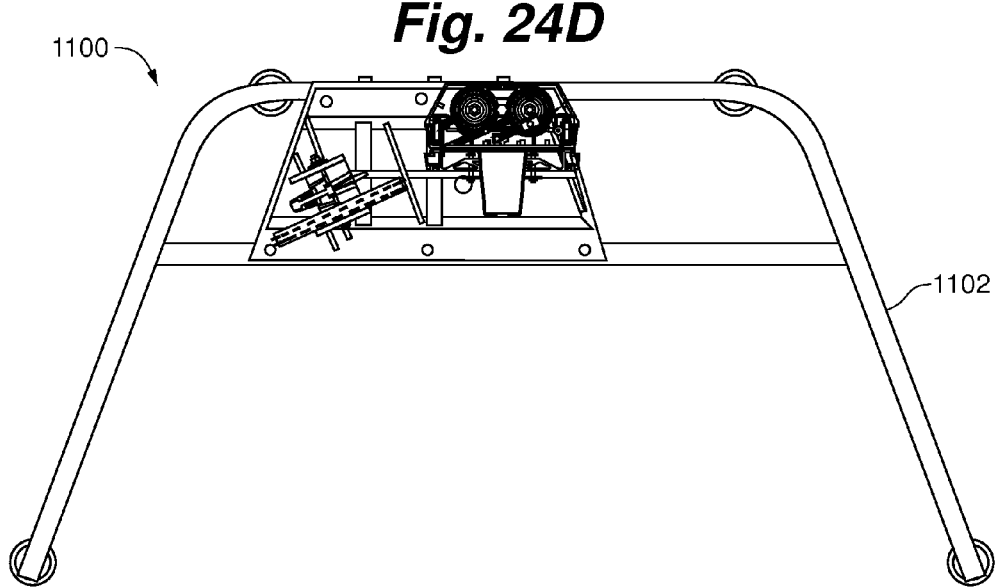
FIG. 24D is a partial top view of the height adjustable desk of FIG. 24A in accordance with an embodiment of the invention.
Figure 24E:
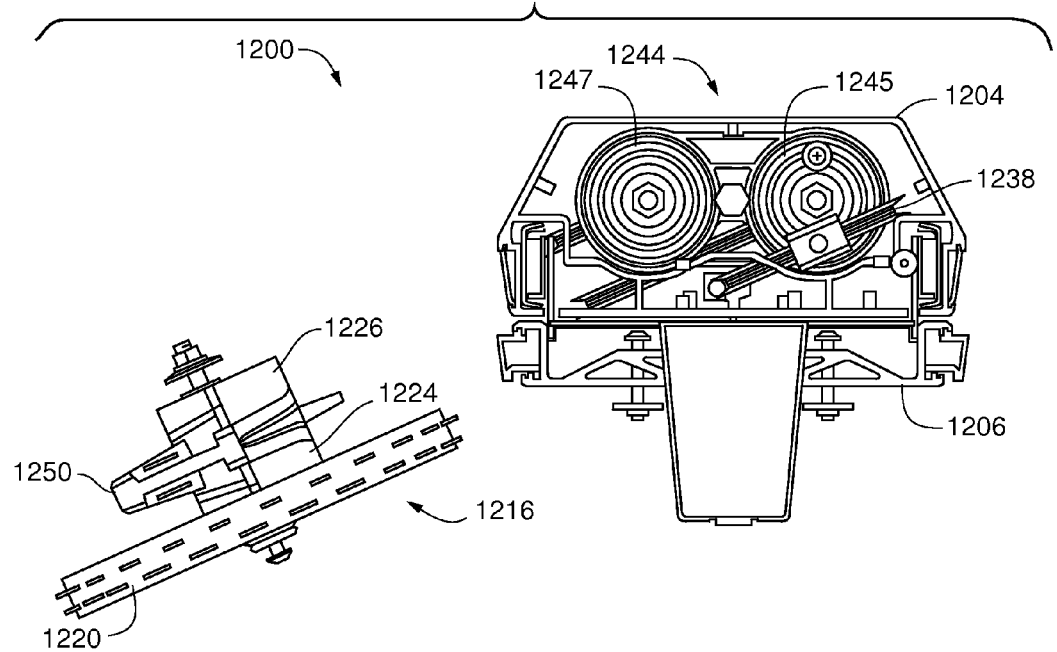
FIG. 24E is a partial top view of a lift mechanism of the height adjustable desk of FIG. 24A in accordance with an embodiment of the invention.

FIG. 24D is a partial top view of the height adjustable desk 1100 the balance mechanism housing 1208 removed, and FIG. 24E is a partial top view of the lift mechanism 1200. In this embodiment the lift mechanism 1200 is similar to the lift mechanism shown in FIGS. 22A-22C and operates in much the same way. For example, the lift mechanism 1200 includes a support column 1204 and a mounting portion 1206, which in this case comprises a flat planar member as opposed to the three-sided member shown in FIGS. 22A-22C. The energy storage member 1244 comprises a first extension spring 1245 and a second extension spring 1247. The lift mechanism 1200 also includes a balance mechanism coupled between the mounting portion 1206 and the energy storage member 1244 for balancing forces between the energy storage member 1244 and the mounting portion 1206. The balance mechanism 1216 similar to the balance mechanism 116 described above with respect to FIGS. 1-9 and includes a wheel 1220 that is rotationally coupled to a cam member 1250 that includes a first cam 1224 and a second cam 1226. A pulley system 1230 includes a first cam pulley that routes a first flexible element (not shown) that is coupled at one end to the first cam 1224 and at the other end to the first extension spring 1245. A second cam pulley 1268 routes a second flexible element (not shown) that is coupled at one end to the second cam 1226 and at the other end to the second extension spring 1247. A third flexible element (also not shown) is coupled between the wheel 1220 and the mounting portion 1206. Two direction-changing pulleys including a lower pulley and an upper pulley 1238 route the third flexible element between the mounting portion 1206 and the wheel 1220. Operation of the balance mechanism 1216 occurs in a manner similar to the example in FIGS. 22A-22C, with the cam member 1250 converting a variable force from the two extension springs 1245, 1247 into a substantially constant force for the mounting portion 1206.

As described herein, a number of positioning apparatuses and height adjustable desks can incorporate a balance mechanism having two or more cams. Also, a number of examples of positioning apparatuses that may include a balance mechanism having multiple cams is described in co-pending U.S. patent application Ser. No. 13/191,170, designated by titled Display Positioning Apparatus and Method, and filed concurrently herewith. The entire content of the 13/191,170 application is hereby incorporated by reference herein in its entirety. While it is believed that a multi-cam balance mechanism can provide advantages in certain circumstances, embodiments of the invention are not limited to multi-cam balance mechanisms and may alternatively include a single cam balance mechanism. For example, the positioning apparatuses 300, 400, and 450 shown in FIGS. 12A-13B and 16A-17 could incorporate a lift mechanism including a single cam balance mechanism. In addition, embodiments of the invention include the lift mechanisms and height adjustable desks shown in FIGS. 18A-24B incorporating a single cam balance mechanism as an alternative to a multi-cam (e.g., dual cam) balance mechanism. A single-cam balance mechanism can be any suitable mechanism known in the art. In some embodiments, a single-cam balance mechanism includes a mechanism such as one of those taught in presently co-owned US Patent Application Publication US 2006/0185563 A1, which application was filed Sep. 28, 2005, the entire contents of which is incorporated by reference herein.

In addition, several optional accessories and/or features can be incorporated into any of the lift mechanisms, positioning apparatuses, and/or height adjustable desks described herein. Several examples of features and accessories will now be described.

According to some embodiments, a lift mechanism for a positioning apparatus includes a base that is configured to sit directly on a work surface, such as a desk or table. In certain cases the base is configured to attach (e.g., removably or fixedly) to the work surface. In some cases a positioning apparatus includes one or more mounting brackets (e.g., a cross bar, etc.) configured to attach various pieces of equipment to the lift mechanism. One embodiment includes a small independent work surface attached to the moving portion of a lift mechanism separate from a keyboard tray. One embodiment includes a mount for an electronic display and a keyboard tray configured to support a keyboard. In some cases the lift mechanism is configured to move the display mount and the keyboard tray in tandem. The display mount may be fixed relative to the keyboard tray or there may be an independent lift mechanism for changing the vertical distance between the display mount and the keyboard tray. In some embodiments the keyboard tray is fixed, while in certain cases it may be configured to fold back in order to provide more space for an operator when the keyboard is not in use. In some embodiments the keyboard tray is configured as a larger work surface which can also be used for writing, reading, etc. In addition, in some embodiments the keyboard tray may be fixed in a horizontal relationship with respect to a display mount. Alternatively, the keyboard tray may be attached to a horizontally moving bracket to vary the horizontal distance between the display mount and the operator. In some embodiments the lift mechanism is configured to counter balance the combined weight of any moving portions of the lift mechanism along with any attached equipment. In some embodiments the counter balancing force is adjustable by the operator.

According to some embodiments, a height adjustable desk is configured to position the desk surface in both a sitting position and a standing position to provide a sit-to-stand desk. In some embodiments, the desk surface can be adjusted by about 14-20 inches in order to provide sit-to-stand capability. According to some embodiments, the weight of the desk surface and any equipment located on the desk surface is counterbalanced by using one or more lift mechanisms, thereby providing lift assistance to an operator and lowering the forces needed to adjust the height of the desk surface. In some cases one or more of the lift mechanisms are weight adjustable to increase or decrease the counter balance force in order to more closely match the weight of the desk and any equipment on the desk. According to some embodiments, one or more lift mechanisms can be attached to the bottom of the desk surface at one or more locations, including side edges, corners, a back edge, or away from edges toward the center of the desk surface. Any suitable equipment can be supported by the desk surface, including but not limited to, a computing device, a notebook, a desk stand or arm to hold a number of monitors, a telephone, a document holder, and any other items known in the art.

In certain embodiments, a height adjustable desk can include one of many types of lift mechanisms, including those with a telescoping, non-telescoping, and/or pseudo-telescoping configuration. In some cases a balance mechanism can be located within a riser (e.g., support column), adjacent to the riser, under a work surface, or inside the base with a guide system located on the riser. In some cases a balance mechanism includes a rotary cam member coupled with an energy storage member that includes one or more springs. Many types of springs can be used, including extension springs, compression springs, torsion springs, and/or spiral springs. The guide system that couples a mounting portion to a support column can include one or more slides in each riser or may include rollers. The guide system can be oriented in various directions, including forward facing, sideways, or at any angle in between. In some cases a relatively strong attachment structure (e.g., a bracket) attaches a riser and guide system to a desk surface, thus reducing or eliminating the need for synchronizing multiple risers and guide systems.

According to some embodiments, a height adjustable desk may include a display mount attachment and/or a keyboard tray attachment. In some cases, the display mount attachment can be a height adjustable or fixed height free standing display stand that sits upon the desk surface. In some cases the display mount attachment includes a clamp on arm that could be height adjustable or fixed height. In some cases the display mount attachment is attached to the work surface with one or more fasteners (e.g., bolts, screws, etc.) In addition, any display mount attachment can be configured for one, two, three, or more electronic displays, or may be configured for one or more displays and/or a notebook computer. A keyboard tray attachment can in some cases be clamped on to the work surface, or may be fixedly attached with screws, bolts, etc. In some embodiments, such as those shown above, the work surface may include openings that enable cable management. Some embodiments also include a brake system incorporating a brake mechanism and a brake lever coupled by a cable. The brake lever can be located in any suitable location and may be hand or foot actuated. In certain cases the base of a height adjustable desk includes height adjustable feet or casters. In certain embodiments, the desk may also include one or more of a document holder, a telephone holder, and a computer case holder.

Embodiments of the invention also include methods of positioning equipment, such as a display, keyboard, and/or work surface. According to one embodiment, a method of positioning a display includes lifting a display within a vertical range of travel and assisting the lifting of the display with a variable force exerted by an energy storage member. In some cases the method also includes converting the variable force exerted by the energy storage member into a substantially constant force applied to the display with a balance mechanism. The balance mechanism can comprise any of the balance mechanisms described herein. In one embodiment, the balance mechanism comprises a first cam, a second cam rotationally coupled to the first cam, and a wheel rotationally coupled to the first cam and the second cam. The first cam and the second cam are configured to convert the variable force exerted by the energy storage member into a substantially constant force applied to the display. Such a method can be carried out by articulating any of the lift mechanisms, display positioning apparatuses, and height adjustable desks described herein.

In some embodiments, a method also includes lowering the display within the vertical range of travel and resisting the lowering of the display with an additional variable force exerted by the energy storage member. In this case, the first cam and the second cam are configured to convert the additional variable force exerted by the energy storage member into a substantially constant force applied to the display. For example, as the energy storage member 144 of FIG. 109 contracts, it provides a variable force that resists movement of the mounting portion of the lift mechanism. According to some embodiments, converting the variable force to a substantially constant forces allows the position of the display within the vertical range of travel to be maintained without a brake mechanism.

Moving a display can occur in any suitable manner depending upon the configuration of the lift mechanism (e.g., corresponding to those mechanisms described above.). In some embodiments, lifting the display comprises moving a mounting portion relative to a support column. In certain cases, moving the mounting portion relative to the support column includes moving an inner tube within and relative to an outer tube, such as in the example of a telescoping lift mechanism shown in FIGS. 20A-21D. In some cases, the display may be positioned on or attached to a movable work surface (e.g., as part of a height adjustable desk) and moving the display including moving the movable work surface relative to the support column.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A lift mechanism, comprising:
  a base;
  a support column coupled to the base;
  a mounting portion movably coupled to the support column;
  an energy storage member coupled to the support column; and
  a balance mechanism coupled between the energy storage member and the mounting portion, the balance mechanism comprising:
    a first cam having a profile of radius variation as a function of rotation,
    a second cam rotationally fixed to the first cam, wherein the second cam is a mirror image of the first cam, and wherein the second cam has the same profile of radius variation as a function of rotation as the first cam, and
    a wheel rotationally coupled to the first cam and the second cam, wherein the first cam and the second cam are configured to convert a variable force exerted by the energy storage member into a substantially constant force applied to the mounting portion.

2. The lift mechanism of claim 1, wherein the first cam, the second cam and the wheel are coaxially mounted to the base.

3. The lift mechanism of claim 1, further comprising a cam member comprising the first cam and the second cam.

4. The lift mechanism of claim 1, wherein the first cam and the second cam each comprise a cam surface that winds about the axis of rotation, and wherein the radius of each of the first cam and the second cam decreases as the cam surface winds between a perimeter of the cam and the rotational axis of the cam, wherein the decreasing radius is configured to match a variable force profile of the energy storage member.

5. The lift mechanism of claim 1, wherein the balance mechanism further comprises a pulley system, the pulley system comprising a first cam pulley and a second cam pulley that route one or more flexible elements between the first and the second cams and the energy storage member.

6. The lift mechanism of claim 5, wherein the pulley system further comprises an energy storage member pulley, wherein the first cam pulley, the second cam pulley, and the energy storage member pulley are rotationally coupled, further comprising at least one flexible element coupling the first cam pulley to the first cam and the second cam pulley to the second cam, and further comprising at least one additional flexible element coupling the energy storage member pulley with the energy storage member.

7. The lift mechanism of claim 6, wherein the first cam pulley, the second cam pulley and the energy storage member pulley are integrally formed.

8. The lift mechanism of claim 6, wherein the at least one flexible element coupling the first cam pulley to the first cam and the second cam pulley to the second cam comprises a first flexible element coupling the first cam pulley to the first cam and a second flexible element coupling the second cam pulley to the second cam.

9. The lift mechanism of claim 5, wherein the one or more flexible elements comprises a first flexible element coupled between the first cam and the energy storage member and a second flexible element coupled between the second cam and the energy storage member.

10. The lift mechanism of claim 9, wherein the energy storage member comprises a first extension spring and a second extension spring, and wherein the first flexible element couples to the first extension spring to the first cam and the second flexible element couples the second extension spring to the second cam.

11. The lift mechanism of claim 5, wherein the first cam receives about half of the variable force exerted by the energy storage member on the first cam pulley and the second cam receives about half of the variable force exerted by the energy storage member on the second cam pulley.

12. The lift mechanism of claim 1, wherein the mounting portion comprises a tubular configuration that fits about the support column.

13. The lift mechanism of claim 1, wherein the support column comprises a first tube and the mounting portion comprises a second tube in sliding engagement with the first tube.

14. The lift mechanism of claim 13, wherein the first tube is an outer tube and the second tube is an inner tube received within the outer tube.

15. The lift mechanism of claim 1, further comprising an adjustment mechanism configured to adjust a tension of the energy storage member.

16. The lift mechanism of claim 1, further comprising a brake mechanism coupled to the support column and configured to hold a position of the mounting portion relative to the support column.

17. A display positioning apparatus comprising:
  a base;
  a support column coupled to the base;
  a mounting portion movably coupled to the support column, the mounting portion comprising a display mount for attaching an electronic display;
  an energy storage member coupled to the support column; and
  a balance mechanism coupled between the energy storage member and the mounting portion, the balance mechanism comprising:
    a first cam having a profile of radius variation as a function of rotation,
    a second cam rotationally fixed to the first cam, wherein the second cam is a mirror image of the first cam, and wherein the second cam has the same profile of radius variation as a function of rotation as the first cam, and
    a wheel rotationally coupled to the first cam and the second cam, wherein the first cam, the second cam and the wheel are coaxially mounted to the base and the first cam and the second cam are configured to convert a variable force exerted by the energy storage member into a substantially constant force applied to the mounting portion.

18. The display positioning apparatus of claim 17, further comprising a cam member comprising the first cam and the second cam.

19. The display positioning apparatus of claim 17, wherein the first cam and the second cam each comprise an axis of rotation and a cam surface that winds about the axis of rotation, and wherein the radius of each of the first cam and the second cam decreases as the cam surface winds between a perimeter of the cam and the rotational axis of the cam, wherein the decreasing radius is configured to match a variable force profile of the energy storage member.

20. The display positioning apparatus of claim 17, wherein the balance mechanism further comprises a pulley system, the pulley system comprising a first cam pulley, a second cam pulley, and an energy storage member pulley, wherein the first cam pulley, the second cam pulley, and the energy storage member pulley are integrally formed about a single axis of rotation.

21. The display positioning apparatus of claim 17, wherein the mounting portion further comprises a keyboard tray configured to support a keyboard.

22. The display positioning apparatus of claim 21, wherein the mounting portion comprises a second lift mechanism configured to move the display mount vertically relative to the keyboard tray.

23. The display positioning apparatus of claim 17, wherein the mounting portion comprises at least one of a mouse tray, a document holder, a movable work surface, and a telephone holder.

24. The display positioning apparatus of claim 17, wherein the mounting portion comprises a plurality of display mounts for attaching a corresponding plurality of electronic displays to the mounting portion.

25. The display positioning apparatus of claim 24, wherein at least one of the plurality of display mounts further comprises a tilt mechanism and/or a rotation mechanism.

26. The display positioning apparatus of claim 17, wherein the mounting portion comprises a notebook tray and/or a notebook docking station.

27. A height adjustable desk, comprising:
a base;
a work surface; and
at least one lift mechanism coupled between the base and the work surface, the at least one lift mechanism comprising:
  a support column coupled to the base,
  a mounting portion movably coupled to the support column and fixedly coupled to the work surface,
  an energy storage member coupled to the support column, and
  a balance mechanism coupled between the energy storage member and the mounting portion, the balance mechanism comprising:
    a first cam having a profile of radius variation as a function of rotation,
    a second cam rotationally fixed to the first cam, wherein the second cam is a mirror image of the first cam, and wherein the second cam has the same profile of radius variation as a function of rotation as the first cam, and
    a wheel rotationally coupled to the first cam and the second cam, wherein the first cam and the second cam are configured to convert a variable force exerted by the energy storage member into a substantially constant force applied to the mounting portion.

28. The height adjustable desk of claim 27, further comprising a cam member comprising the first cam and the second cam.

29. The height adjustable desk of claim 28, wherein the cam member comprises an axis of rotation and the first cam and the second cam are symmetrically formed about a plane perpendicular to the axis of rotation.

30. The height adjustable desk of claim 27, wherein the first cam and the second cam each comprise an axis of rotation and a cam surface that winds about the axis of rotation, and wherein the radius of each of the first cam and the second cam decreases as the cam surface winds between a perimeter of the cam and the rotational axis of the cam, wherein the decreasing radius is configured to match a variable force profile of the energy storage member.

31. The height adjustable desk of claim 27, wherein the balance mechanism further comprises a pulley system, the pulley system comprising a first cam pulley, a second cam pulley, and an energy storage member pulley, wherein the first cam pulley, the second cam pulley, and the energy storage member pulley are integrally formed about a single axis of rotation.

32. The height adjustable desk of claim 27, wherein the mounting portion is fixedly coupled to the work surface proximate an edge of the work surface.

33. The height adjustable desk of claim 27, wherein the mounting portion is fixedly coupled to the work surface proximate a center of the work surface.

34. The height adjustable desk of claim 33, wherein the support column comprises a first tube and the mounting portion comprises a second tube in sliding engagement with the first tube.

35. The height adjustable desk of claim 27, wherein the at least one lift mechanism comprises a first lift mechanism and a second lift mechanism.

36. A method of positioning a display, comprising:
assisting a lifting of the display within a vertical range of travel with a variable force exerted by an energy storage member; and
converting the variable force exerted by the energy storage member into a substantially constant force applied to the display with a balance mechanism comprising;
  a first cam having a profile of radius variation as a function of rotation,
  a second cam rotationally fixed to the first cam, wherein the second cam is a mirror image of the first cam, and wherein the second cam has the same profile of radius variation as a function of rotation as the first cam, and
  a wheel rotationally coupled to the first cam and the second cam, wherein the first cam and the second cam are configured to convert the variable force exerted by the energy storage member into the substantially constant force applied to the display.

37. The method of claim 36, further comprising:
resisting a lowering of the display with an additional variable force exerted by the energy storage member, the first cam and the second cam configured to convert the additional variable force exerted by the energy storage member into a substantially constant force applied to the display.

38. The method of claim 36, further comprising:
-maintaining a position of the display within the vertical range of travel with the balance mechanism and the energy storage member.

39. The method of claim 36, wherein lifting the display comprises moving a mounting portion relative to a support column.

40. The method of claim 39, wherein moving the mounting portion relative to the support column comprises moving an inner tube within and relative to an outer tube.

41. The method of claim 36, wherein lifting the display comprises moving a movable work surface relative to a support column.

\* \* \* \* \*